United States Patent
Wei et al.

(10) Patent No.: US 6,489,153 B1
(45) Date of Patent: Dec. 3, 2002

(54) ISOLATED HUMAN KINASE PROTEINS, NUCLEIC ACID MOLECULES ENCODING HUMAN KINASE PROTEINS, AND USES THEREOF

(75) Inventors: Ming-Hui Wei, Rockville, MD (US); Karen A. Ketchum, Rockville, MD (US); Ellen M. Beasley, Rockville, MD (US); Valentina DiFrancesco, Rockville, MD (US)

(73) Assignee: PE Corporation (NY), Norwalk, CT (US)

( * ) Notice: Subject to any disclaimer, the term of this patent is extended or adjusted under 35 U.S.C. 154(b) by 0 days.

(21) Appl. No.: 09/984,880

(22) Filed: Oct. 31, 2001

(51) Int. Cl.[7] .............................. C12N 9/12; C12N 1/20; C12N 15/00; C12N 5/00; C07H 21/04
(52) U.S. Cl. .................... 435/194; 435/320.1; 435/325; 435/252.3; 435/6; 536/23.2
(58) Field of Search .............................. 435/194, 320.1, 435/325, 252.3, 6; 536/23.2

(56) References Cited

PUBLICATIONS

Kawai et al., Nature, 409, 685–690, 2001.*

\* cited by examiner

Primary Examiner—M Monshipouri
(74) Attorney, Agent, or Firm—Celera Genomics; Justin Karjala

(57) ABSTRACT

The present invention provides amino acid sequences of peptides that are encoded by genes within the human genome, the kinase peptides of the present invention. The present invention specifically provides isolated peptide and nucleic acid molecules, methods of identifying orthologs and paralogs of the kinase peptides, and methods of identifying modulators of the kinase peptides.

9 Claims, 17 Drawing Sheets

```
   1 CGGGGCCGAG GGCGGCGTCG CTGAGGCGCC CATGGCCTTC GCCCGCCGGC
  51 TCCTGCGCGG GCCACTGTCG GGGCCGCTGC TCGGCGGCG CGGGGTCTGC
 101 GCTGGGGCCA TGGCTCCGCC GTGCCGCTTC GTCCTGGAGC TTCCCGACTG
 151 CACCCTGGCT CACTTCGCCC TAGGCGCCGA CGCCCCCGGC GACGCAGACG
 201 CCCCCGACCC CCGCCTGGCG GCGCTGTTGG GGCCCCCGGA GCGCAGCTAC
 251 TCGCTGTGCG TGCCCGTGAC CCCGGACGCC GGCTGCGGGG CCCGGGTCCG
 301 GGCGGCGCGG CTGCACCAGC GCCTGCTGCA CCAGCTGCGC CGCGGCCCCT
 351 TCCAGCGGTG CCAGCTGCTC AGGCTGCTCT GCTACTGCCC GGGCGGCCAG
 401 GCCGGCGGCG CACAGCAAGG CTTCCTGCTG CGCGACCCCC TGGATGACCC
 451 TGACACCCGG CAAGCGCTGC TCGAGCTGCT GGGCGCCTGC CAGGAGGCAC
 501 CACGCCCGCA CTTGGGCGAG TTCGAGGCCG ACCCGCGCGG CCAGCTGTGG
 551 CAGCGCCTCT GGGAGGTGCA AGACGGCAGG CGGCTGCAGG TGGGCTGCGC
 601 ACAGGTCGTG CCCGTCCCGG AGCCCCCGCT GCACCCGGTG GTGCCAGACT
 651 TGCCCAGTTC CGTGGTCTTC CCGGACCGGG AAGCCGCCCG GCCGTTTTG
 701 GAGGAGTGTA CCTCCTTTAT TCCTGAAGCC CGGGCAGTGC TTGACCTGGT
 751 CGACCAGTGC CCAAAACAGA TCCAGAAAGG AAAGTTCCAG GTTGTTGCCA
 801 TCGAAGGACT GGATGCCACG GGTAAAACCA CGGTGACCCA GTCAGTGGCA
 851 GATTCACTTA AGGCTGTCCT CTTAAAGTCA CCACCCTCTT GCATTGGCCA
 901 GTGGAGGAAG ATCTTTGATG ATGAACCAAC TATCATTAGA AGAGCTTTTT
 951 ACTCTTTGGG CAATTATATT GTGGCCTCCG AAATAGCTAA AGAATCTGCC
1001 AAATCTCCTG TGATTGTAGA CAGGTACTGG CACAGCACGG CCACCTATGC
1051 CATAGCCACT GAGGTGAGTG GGGGTCTCCA GCACCTGCCC CCAGCCCATC
1101 ACCCTGTGTA CCAGTGGCCA GAGGACCTGC TCAAACCTGA CCTTATCCTG
1151 CTGCTCACTG TGAGTCCTGA GGAGAGGTTG CAGAGGCTGC AGGGCCGGGG
1201 CATGGAGAAG ACCAGGGAAG AAGCAGAACT TGAGGCCAAC AGTGTGTTTC
1251 GTCAAAAGGT AGAAATGTCC TACCAGCGGA TGGAGAATCC TGGCTGCCAT
1301 GTGGTTGATG CCAGCCCCTC CAGAGAAAAG GTCCTGCAGA CAGTATTAAG
1351 CCTAATCCAG AATAGTTTTA GTGAACCGTA GTTACTCTGG CCAGGTGCCA
1401 CGTCTAACTA GATTAGATGT TGTTTGAAAC ATCTACATCC ACCATTTGTT
1451 ATGCAGTGTT CCCAAATTTC TGTTCTACAA GCATGTTGTG TGGCAGAAAA
1501 CTGGAGACCA GGCATCTTAA TTTTACTTCA GCCATCGTAC CCTCTTCTGA
1551 CTGATGGACC CGTCATCACA AGGTCCCTC TCATCATGTT CCAGTGAGAG
1601 GCCAGCGATT GCTTTCTTCC TGGCATAGTA AACATTTTCT TGGAACATAT
1651 GTTTCACTTA ATCACTACCA AATATCTGGA AGACCTGTCT TACTCAGACA
1701 GCACCAGGTG TACAGAAGCA GCAGACAAGA TCTTCCAGAT CAGCAGGGAG
1751 ACCCCGGAGC CTCTGCTTCT CCTACACTGG CATGCTGATG AGATCGTGAC
1801 ATGCCCACAT TGGCTTCTTC CACATCTGGT TGCACTCGTC ATGATGGGCT
1851 CGCTGCATCT CCCTCAGTCC CAAATTCTAG TAGCCAAGTG TTCCTGCAGA
1901 GGCTGTCTAT GTGTCCTGGC TGCCCAAGGG ACACTCCTGC AGAGCCATTT
1951 TTGGGTAAGG AACACTTACA AAGAAGGCAT TGATCTTGTG TCTGAGGCTC
2001 AGAGCCCTTT TGATAGGCTT CTGATGTCAT TCATAAAGAC ATTCAAGCCA
2051 AGATGCTCCA ACTGCAAATA TACCAACCTT CTCTGAATTA TATTTTGCTT
2101 ATTTATATTT CTTTTCTTTT TTTCTAAAGA ATTGGCTCTG AATAGAATGC
2151 ACATTTTCCA TCTGAACTGG ATGCATATCA TTTAGCCAAT CCAGTAATTT
2201 ATTTATATTA ATCTATACAT AATATGTTTC CTCAGCATAG GAGCTATGAT
2251 TCATTAATTA AAAGTGGAGT CAAAACGCTA AATGCAATGT TTGTTGTGTA
2301 TTTTCATTAC ACAAACTTAA TTTGTCTTGT TAAATAAGTT CAAGTGGATC
2351 TTGGAGTGGG ATTTCTTGGT AAATTATCTT GCACTTGAAT GTCTCATGAT
2401 TACATATGAA ATCGCTTTGA CATATCTTTA GACAGAAAAA AGTAGCTGAG
2451 TGAGGGGGAA ATTATAGAGC TTGTGTGACT TTAGGGAGTA GCTGTCTCTT
2501 ATACACATAC TCAAGCCCTG AAGCCTTGCA TGTCCTGCAG CGTCGCACTA
2551 AAGGAGGGGG CTTTTGCACC C
       (SEQ ID NO: 1)
```

FIG.1A

FEATURES:
5'UTR:        1 - 31
Start Codon:  32
Stop Codon:   1379
3'UTR:        1382

Homologous proteins:

Sequences producing significant alignments:                         Score    E
Value                                                               (bits)

CRA|98000043611838  /altid=gi|12835871 /def=dbj|BAB23396.1| (AKO...   608   e-173
CRA|18000004977190  /altid=gi|10181118 /def=ref|NP_065582.1| thy...   262   1e-68
CRA|335001098644584 /altid=gi|11466103 /def=ref|NP_047035.1| TK...    116   1e-24
CRA|67000041026087  /altid=gi|13562008 /def=gb|AAK30607.1|AF3502...    81   6e-14
CRA|18000004875826  /altid=gi|115398   /def=sp|P17656|CC02_CAEEL C... 80   1e-13
CRA|67000041026083  /altid=gi|13562004 /def=gb|AAK30605.1|AF3502...    80   2e-13
CRA|18000004994956  /altid=gi|71405    /def=pir||CGCH1S collagen al... 78   4e-13
CRA|18000004942943  /altid=gi|115268   /def=sp|P02457|CA11_CHICK C... 78   4e-13
CRA|271274599       /altid=gi|7801278  /def=emb|CAB91142.1| (AL355913)... 78 4e-13
CRA|18000005169791  /altid=gi|3641659  /def=dbj|BAA33381.1| (AB00...   77   9e-13 dbEST:

CRA Number              gi Number    Score       Expect
-----------             ---------    -----       ------
CRA|157000141080761     gi|13462554  1360 bits  (686)   0.0
CRA|78000169053550      gi|14048666  1273 bits  (642)   0.0
CRA|78000169051306      gi|14048462  1221 bits  (616)   0.0
CRA|155000041537799     gi|10162440  1193 bits  (602)   0.0
CRA|156000152698673     gi|11155283  1154 bits  (582)   0.0
CRA|156000152689550     gi|11154451  1146 bits  (578)   0.0
CRA|78000169034399      gi|14046924  1118 bits  (564)   0.0
CRA|224000004311810     gi|15928374  1102 bits  (556)   0.0
CRA|157000141097724     gi|13462915  1063 bits  (536)   0.0
CRA|78000169034718      gi|14046953  1059 bits  (534)   0.0
CRA|155000041535193     gi|10162203  1045 bits  (527)   0.0
CRA|58000098794394      gi|12765577  969 bits   (489)   0.0

EXPRESSION INFORMATION FOR MODULATORY USE:

| gi Number | Organ | Tissue Type |
|---|---|---|
| gi|13462554 | prostate | adenocarcinoma |
| gi|14048666 | prostate | adenocarcinoma |
| gi|14048462 | prostate | adenocarcinoma |
| gi|10162440 | bone marrow | from acute myelogenous leukemia |
| gi|11155283 | bone marrow | from acute myelogenous leukemia |
| gi|11154451 | bone marrow | from acute myelogenous leukemia |
| gi|14046924 | lung | mucoepidermoid carcinoma |
| gi|15928374 | pooled brain, lung, testis | (none) |
| gi|13462915 | prostate | adenocarcinoma |
| gi|14046953 | lung | mucoepidermoid carcinoma |
| gi|10162203 | bone marrow | from acute myelogenous leukemia |

FIG.1B gi|12765577    prostate                adenocarcinoma, cell line

Tissue expression:
Pooled: Brain, Heart, Kidney, Lung, Spleen, Testis, Leukocyte

FIG.1C

```
  1 MAFARRLLRG PLSGPLLGRR GVCAGAMAPP CRFVLELPDC TLAHFALGAD
 51 APGDADAPDP RLAALLGPPE RSYSLCVPVT PDAGCGARVR AARLHQRLLH
101 QLRRGPFQRC QLLRLLCYCP GGQAGGAQQG FLLRDPLDDP DTRQALLELL
151 GACQEAPRPH LGEFEADPRG QLWQRLWEVQ DGRRLQVGCA QVVPVPEPPL
201 HPVVPDLPSS VVFPDREAAR AVLEECTSFI PEARAVLDLV DQCPKQIQKG
251 KFQVVAIEGL DATGKTTVTQ SVADSLKAVL LKSPPSCIGQ WRKIFDDEPT
301 IIRRAFYSLG NYIVASEIAK ESAKSPVIVD RYWHSTATYA IATEVSGGLQ
351 HLPPAHHPVY QWPEDLLKPD LILLLTVSPE ERLQRLQGRG MEKTREEAEL
401 EANSVFRQKV EMSYQRMENP GCHVVDASPS REKVLQTVLS LIQNSFSEP
    (SEQ ID NO: 2)
```

FEATURES:
Functional domains and key regions:

PDOC00005 PS00005 PKC_PHOSPHO_SITE
Protein kinase C phosphorylation site
Number of matches: 3
    1   263-265    TGK
    2   275-277    SLK
    3   322-324    SAK

---

PDOC00006 PS00006 CK2_PHOSPHO_SITE
Casein kinase II phosphorylation site
Number of matches: 4
    1   271-274    SVAD
    2   378-381    SPEE
    3   394-397    TREE
    4   445-448    SFSE

---

PDOC00007 PS00007 TYR_PHOSPHO_SITE
Tyrosine kinase phosphorylation site
        407-414    RQKVEMSY

---

PDOC00008 PS00008 MYRISTYL
N-myristoylation site
Number of matches: 4
    1   21-26     GVCAGA
    2   121-126   GGQAGG
    3   259-264   GLDATG
    4   390-395   GMEKTR

---

PDOC00009 PS00009 AMIDATION
Amidation site
Number of matches: 2
    1   17-20     LGRR
    2   181-184   DGRR

---

PDOC00017 PS00017 ATP_GTP_A
ATP/GTP-binding site motif A (P-loop)
        259-266    GLDATGKT

FIG. 2A

Membrane spanning structure and domains:

| Helix | Begin | End | Score | Certainty |
|---|---|---|---|---|
| 1 | 274 | 294 | 1.133 | Certain |
| 2 | 489 | 509 | 1.775 | Certain |

BLAST Alignment to Top Hit:
Alignment to top blast hit:

>CRA|18000004977190 /altid=gi|10181118 /def=ref|NP_065582.1|
thymidylate kinase family LPS-inducible member;
thymidylate kinase homologue [Mus musculus] /org=Mus
musculus /taxon=10090 /dataset=nraa /length=431
Length = 431

Score = 262 bits (663), Expect = 1e-68
Identities = 133/192 (69%), Positives = 152/192 (78%), Gaps = 5/192 (2%)
Frame = +2

Query: 704
ECTSFIPEARAVLDLVDQCPKQIQKGKFQVVAIEGLDATGKTTVTQSVADSLKAVLLKSP 883
 +CTSFIPEARAVLDLVDQCPK++QKGKFQV+AIEGLDATGKTT+TQ       +
Sbjct: 157
QCTSFIPEARAVLDLVDQCPKEVQKGKFQVIAIEGLDATGKTTLTQHFKSLSRLSSYSRH 216

Query: 884   PSCIGQWRKIFDDEPTIIR-----
RAFYSLGNYIVASEIAKESAKSPVIVDRYWHSTATY 1048
          P CI    K  +++  ++        F    NY+VASEIAKES
PVIVDRYWHSTATY
Sbjct: 217   PPCI----
KPVEEDLLMMNLLSFEEPFILWANYLVASEIAKESTNFPVIVDRYWHSTATY 272

Query: 1049
AIATEVSGGLQHLPPAHHPVYQWPEDLLKPDLILLLTVSPEERLQRLQGRGMEKTREEAE 1228
           AIATEVSGGLQ+LPPAHHPVYQWP DLLKPDL+LLLTV+ EER++RLQGRG
EKT+EEAE
Sbjct: 273
AIATEVSGGLQYLPPAHHPVYQWPGDLLKPDLVLLLTVNSEERVRRLQGRGQEKTKEEAE 332

Query: 1229 LEANSVFRQKVE 1264
            LEAN+VFRQKVE
Sbjct: 333   LEANNVFRQKVE 344 (SEQ ID NO: 4)

SignalP results:

< Is the sequence a signal peptide?

| # Measure | Position | Value | Cutoff | Conclusion |
|---|---|---|---|---|
| max. C | 49 | 0.362 | 0.37 | NO |
| max. Y | 49 | 0.220 | 0.34 | NO |
| max. S | 4 | 0.884 | 0.88 | YES |
| mean S | 1-48 | 0.369 | 0.48 | NO |

FIG. 2B

Most likely cleavage site between pos. 48 and 49: ALG-AD

Hmmer search results (Pfam):
Scores for sequence family classification (score includes all domains):

| Model | Description | Score | E-value | N |
|-------|-------------|-------|---------|---|
| PF02223 | Thymidylate kinase | 50 | 1.6e-12 | |
| PF01712 | Deoxynucleoside kinase | 4.0 | 8 | 1 |
| PF00457 | Glycosyl hydrolases family 11 | 3.3 | 8.8 | 1 |

Parsed for domains:

| Model | Domain | seq-f | seq-t | hmm-f | hmm-t | score | E-value |
|-------|--------|-------|-------|-------|-------|-------|---------|
| PF02223 | 1/1 | 257 | 437 .. | 1 | 197 .. | 50 | 1.6e-12 |
| PF00457 | 1/1 | 253 | 270 .. | 177 | 194 .] | 3.3 | 8.8 |
| PF01712 | 1/1 | 359 | 390 .. | 71 | 100 .. | 4.0 | 8 |

FIG. 2C

```
   1 AAAAGTTAGG AAGAAGCTGG TCTTCCTACT TACCCTCAAG GTGCTCAGTG
  51 GTGGGAAATA GACTGGCACG TGACTGTGGA GTGTCAAGGT CCGAGGATAC
 101 AAATAGCCTT GGTGGGGGAC ACAGGAGAGG CTACTAACCC AGATATGTGG
 151 GGGGTTATAG GCTATATCAT GTCCCCCAAA ATTCATGTTC AGGCCTAGCC
 201 CCCAGTGCCT CACAGTATGA CTGTATTTCA AAATAAGCCT TTCAATAGGT
 251 GATTACATTA AAATGAGAAC ATTATGATGG GCCCTAACCC AATCTGACTG
 301 GTGTCCTTCC CAGAAGAGGA AATTTGGAAC TTCAAGGAGA CGCCAAGGAT
 351 GCAAGCACAA AGGAAAGGTC CCGTGAGAAC ACAGAGAGAA GGAGGCGGTC
 401 TGCACGCTAG AAAGAGAGGC CTCAGAAAAA GCAAACCCTG CTGGCAACTT
 451 GATCTCCAGC TTCTCTGGCC ACCTGAACTT TGAGAAAACA AATTTTCTAT
 501 TGTTTAGGCG GCCCAGTCCG TGGTATTTTG TTATGGCAGC CAGGATAGAC
 551 TAATACATCC AGAGAGGTGG ATGGCATAGG GAAAAGGTCA AGCAGGCTTG
 601 AGGATGCAGT ACTGTCTTAG AGAAGAAAAG GGAGTAACTA GAAGACTCTT
 651 ACTTCCATAT ACTACATACA CGTGAAACCA CCGGTACATG CTAAATGTCC
 701 AAAAGTGAAA TTCCTGAGAA AGAATAAAAA CTATTCTATT CTCAAAGAGC
 751 TAAAAAATTT TAAACTCCTA ATTCTTCTTT CTTCTTAGCC TATTAACCCA
 801 CACTCCAACC ACCTATCTAT ATTTCACGTT TGTTAAGACT TTTTTTTTCA
 851 GAATTAAATA TAATCCCAAG TTTAAGTCCA ATACTATTAA GACATAAAAA
 901 AAAAAACTGC TTTCAGCTCA TCTAATGTTT TCAATCTTCG TCTCAATTCT
 951 ATTTTTTTGA GAGAGTTTCC CTGGAGAATA TTATCTTTTT GTTTGTTTTT
1001 GGTTTGCTTG ACATCATTTT TAAAAGGCAT CAGTTAATGA GTAAACACAG
1051 AATAAAATAT CCAAATAACT GCGCAAACAC TGTTACACTG TTAGGCAGTT
1101 ACACTGTTAG GCAGCAACAG TGCTGATGCT GGACTGTGGC AGGCAGAGGG
1151 TGCTATCCTG ACACACTTCA CCTTAGTGCA GGAAACTTCA ATTTGGTGGA
1201 AGAAAGGCGA TTTCGAGGTT CCAATCTGGG CGACACTTCC CAGTTGGAGA
1251 GTCAGCAAAA GGGAGAGGGC AATTCCAAGA AGAGGGAAAA GCTTGTGCAC
1301 AGGTGAGTGT GTGCAAAGGT GAGTGTGTGC ACAGGTGAGT GAGTGCACAG
1351 GTGAGATAAG ATACAGGAGA GGGAAGAGCC AGAACTGCGC CCTGTTCCCG
1401 CAGGAAAGCA GCTCTGCAGG ATTAGAGGGG CGGGGACGCG TGGTCAGAGC
1451 TAGGAGTTGA GGTCGGGGAG GGAGCCCATG GTCTGCAGGG CCTGGTCAGT
1501 CATCCAAGGG CAGTAGTGCG CCTGCAAGTG GGCGTTGAAG AGCCCGTTAC
1551 ACCGGGAAGG GACTTCTCTG TCCCTCGCGC GTGCACCCCC GCCCCCCTCC
1601 ATGCACCCGG CATAAGCCGC AGAGGAGGAA CTCAAACCAG GGTCGGGGCC
1651 GCCAGCCACC CGCAGAACGC ACACGGAGCT ACCTTGGGGC CGACGGCGCG
1701 GGGCCTCATT CGGTGTCAGC CCCGGGAGCC GGCGCCTGGG GACCGCGCAG
1751 GCCCGCGGAG CCGCGCACCT GGGGCCCCGG GGCCAAGCGT CTGCTCCCGA
1801 GCGCCGGCCG TTTATCGCGC ACATCTCGCG GCGAGGAGGA GAGGCCGGAA
1851 GGGCGCCCCA GCCCCAAGGC TCCTGCCCCG CCTGGGCCTC CGGCTTTCGT
1901 TTCCCCGCAA CGCTTCGCTT TCGTTTCCCG CTGGCGCCTG GCTCCCTCCG
1951 GGTTTCGTTT CCCGCCGGCG CCTGGCTCCC GCCAGGTTTC GTTTCCGAGG
2001 CGGGGCCGAG GGCGGCGTCG CTGAGGCGCC CATGGCCTTC GCCCGCCGGC
2051 TCCTGCGCGG GCCACTGTCG GGCCGCTGC TCGGGCGGCG CGGGGTCTGC
2101 GCTGGGGCCA TGGCTCCGCC GCGCCGCTTC GTCCTGGAGC TTCCCGACTG
2151 CACCCTGGCT CACTTCGCCC TAGGCGCCGA CGCCCCCGGC GACGCAGACG
2201 CCCCCGACCC CCGCCTGGCG GCGCTGCTGG GGCCCCGGA GCGCAGCTAC
2251 TCGCTGTGCG TGCCCGTGAC CCCGGACGCC GGCTGCGGGG CCCGGGTCCG
2301 GGCGGCGCGG CTGCACCAGC GCCTGCTGCA CCAGCTGCGC CGCGGCCCCT
2351 TCCAGCGGTG CCAGCTGCTC AGGCTGCTCT GCTACTGCCC GGGCGGCCAG
2401 GCCGGCGGCG CACAGCAAGG CTTCCTGCTG CGCGACCCCC TGGATGACCC
2451 TGACACCCGG CAAGCGCTGC TCAGCTGCT GGGCGCCTGC AGGAGGCAC
2501 CACGCCCGCA CTTGGGCGAG TTCGAGGCCG ACCCGCGCGG CCAGCTGTGG
2551 CAGCGCCTCT GGGAGGTGCA AGACGGCAGG CGGCTGCAGG TGGGCTGCGC
2601 ACAGGTCGTG CCCGTCCCGG AGCCCCGCT GCACCCGGTG GTGCCAGACT
```

FIG.3A

```
2651 TGCCCAGTTC CGTGGTCTTC CCGGACCGGG AAGCCGCCCG GGCCGTTTTG
2701 GAGGAGGTAA GAGTTCTGTC CGCTTCCAGC TCCCAGCGTG GCATCTGAAC
2751 CCTTCAGACC AGAGAACTGG ACCAAGAGGC TGGTCTGTAA AGCCGGTTCT
2801 TGCCTGGGTG GTTTGTTTAT TTCCGTTCAC AAATCAGGTA GGGAAGGTGT
2851 CCTGTATGCC AGGCAACTCT TTTAAGATTC TTGTTTGCAA GGATCTTCCA
2901 ACCTGACGTG GAACATAGAC CTACACCAAG CCACGCGATG CTTGCTGTAA
2951 AAGCATCCCA ACAGCAGTAC AGAGGGAGTA AAGGGGCTGC CGGGAGTGAG
3001 GGAAAATAAT GTCAGCTGGG AAGTAATTTT ATTTGCTGAT GATCACCATT
3051 CAAGGATCTT GGGGTGAAAA AGAAAATGCA TGAGTTTAGG GGGTTTAAGA
3101 AATTTAGACT TAAATAGTGT TTACCTACCG ACTGGCCATG AACCTTGTGC
3151 AGGTTACTCA ACTACTCTAA GTTTTGCCCT TTGACATGTA CAATTCCCAT
3201 CTTGCGATGT TGTCCTGATT AAGGAAACAT CTGACTCACA GCAGGTACCC
3251 ACAGAAAGAG ACTGAAAATT CTTTCTGATC GCAGGCTAGG CAGATGTCCT
3301 CCTGTGACAC AGATGAGCCC TGAGGATGCC CCCATGGATC TTGGGAATAT
3351 TTTCCAAGCT TACGGGACAG CGTTGTGGAG CAGTTAAGAG TGCAAGGTCA
3401 ACCACGTGTA TTTAAATTTA AACTCTGGCA TTTATTAGCT GTGTCACTTT
3451 GAGCAAGTTT CTTCAACTCT CTGCCTCAGT TTCCTTAATT CATATGGTGG
3501 GAATAATAAT AGCACCCCCC CCACCCCAGT TCACAGAGAT TGGCAACTGA
3551 ATACTTGTAA AGCACTTAGA AGATTGCCAT GCTCAGAGCA AGCACATAAG
3601 TGTCTGAGCC TCGCTCTGAG ATGCTGTGAG CGTGCAGTGA GATAATGCAC
3651 ATTGAGGAAC TGGGAATTCC CAGGGGACG CTGCTCTGCC AGCTTCATGA
3701 TTGCAGTGCT TGGCTGTTTA TCTCAGCCCC CTGAATGGCT AGGAGAGGAC
3751 ATGCTGCAGA TGAAGACTGC TCTCTCCAGC CCACTGTGCA GCTGATTTCC
3801 CATTCTTGTG ACACAGTGTT CCCAGCGGGC CTGTAGTTCC ATGGTTGCGG
3851 TGTCACAGGA CATTGTGATG ATGTGCCTTG CCTGGCCTTT CTCAAAGCTG
3901 CTCAGTGAAG GCTGCAGGCC ACCAAGCGAT CCAGACAGGG ACAGCTGTTT
3951 CGAGCCTTGG CTGCTCAATA TAAAATAAAA TACTCCAGTC CATCCTAGCA
4001 TCGAAATACT CTGAATTCCC ATGGCCTGGC ACAGTGCTCA GTATAACTTA
4051 GGCCTTATTA GCATGCGGCA ATATTGTGCT CAGCAATTTA GGTGTGATTT
4101 CTGCAAAAGC CCCCTGGCTT CATTGCTGAT GGATAGACGT TGTTTTACAG
4151 TGTACCTCCT TTATTCCTGA AGCCCGGGCA GTGCTTGACC TGGTCGACCA
4201 GTGCCCAAAA CAGATCCAGA AAGGAAAGTT CCAGGTTGTT GCCATCGAAG
4251 GACTGGATGC CACGGGTAAG ATAATATTAC CTTTTAGTTA TAGGCAATGA
4301 CACTAACTGA TTAGTTGCAG AAACAGAAAT ACTTCCTGCA AAACCAAACT
4351 TTATATGGAG CCTTATGTGT GCCCCTACTG TGTGGCAGGC CCTGTGCTAG
4401 GCAGGCCCTG GGATGCAGAG ATGAATAAGA CCTTCAATAT GAAGCAGCAT
4451 GATGTGTGGG CGCGGATCCT CAGTGCTCTG GCGGAACACA GGAAGGGCAC
4501 TGAATCTGGC CTCTGTGGGG CTTTGTCGGG TGGAGTGCAT GGTCAAGGGT
4551 GATACCTGGA TTGTATTTTA AGTACAGATA GGAGTTGGTC AGGTGATGAA
4601 AGCAGGTAAC ATCCTCCAGA CAGAAGAAAT AGCCTGGGCA AAGGTGCAGG
4651 GGCTTGAACC AGGGTGGTGT GTCCAGGAAC CACAGGCAAT TCAGAGATTC
4701 TTCTGGAGCA AAATGTGGAA GAACTAGGAA ATGGAAGAAA AAAAAGCCTT
4751 CTGAGCTGTC AAACTGAGGT CAAAATATAA TGTGTGCTCA CATGAGACCA
4801 AAGTACAAAA GGGGCAGACA TGCTGCTCCT GTGGCCCAGG ACACACTGAG
4851 GAGAGGGTTG ATGTTGGAGA ACTAGCATCC GAGTGGTTCA GCGTAGGAGT
4901 TTCTCCTCCT GTGTAAACTT GAGGGGTACA GACTTTTAAT AATATAAAAG
4951 GCAATTTCCA TATAGAGGTA CTTGTGAACC CAGCTAGGGA GATGTGGCAC
5001 AGGTGATGGC CCATGTTGAC CATCCTGGCT CCATGTGAAG GAGCGGGCCA
5051 TGTCCTGGCC TTCAGGGAGA CCAGCTGTCA TCACTCAAAT GTACTGGCCG
5101 TGTCCAGGAC CCATCACAGT TTCTTTCAGC TGCAGAGGGA ATTGTAACAC
5151 CATCAATCCT TCAGCTGATG TGTTTTGTTG ATCATTTATT TTGTACCCAC
5201 AGCTAATTTA GATTTGGTGG GATTACAGGA GACATAAAAA TTCAGCCTCA
5251 ACACAAGCAT CCACACATAC AAATGTTACA AGGAGTTAGC ATAGAGTGGC
```

FIG.3B

```
5301 AGAAAGAACA CAGGCTAGTG GTTCCGTCTG CCCTGCATTT GCATCCTGCA
5351 CCAAGGCCTA TCAGGAGGGT GAGTTTGGGT AAATTTATTA ACTTCTCCAG
5401 TGCTCAATTT CTTCTTCTGT CAGATGATTA AATAATAACT GTTTTGCAGA
5451 GTCACTGGGA GAATTAGGAG TATAACGTGC TGAGTACTTG GCTCCTAGCA
5501 GACACTGAGA AATGGTAGCT ACTGTTAGGG TCCGTCCTGA CAACCTAAGA
5551 AAAAAAGAAA ATAGATAGTT GGCAATAAAG TGTTAAGTGT GTGATAGAGA
5601 AACTTAAAAA TAAATCGAAA CAGTAGGAGC TCAGAGAAAC TAGTGCACAG
5651 TGTGCTGGAG TAGATCTTCT CATCACCACC TGTCCTGAGC TCCAGGCAGC
5701 AGCTGAGAAT TGTGAGATGG GCTCTGGGAA GGGACTAATC TGTCACCCGA
5751 GGCTGTGCAA GGGGGAGTCA GAAAGTCAAT GAGGCCTAAG CAGTGCCTTT
5801 GAGGAGAAAG CTGAAGCCTA AAGCAGATAC AAAAGCTCTA AAGGCCAAGG
5851 CCAAGCCCAA AGGGGCAAGC ACAGGAGTGA GTGGTAGAAC CAGGGCTGGA
5901 AATTGGAAAG GGATTGCACA GAAGTGGAAG CAGGGTATGA AGAAGGTAGA
5951 AAGAGAGGAG GGGCGAGAAG AGTTGCTGTG GATGCCAGGT GTGGGTTCAT
6001 CAACTATAGA CAATAAGAGG AGAGAAAGTC TTCTGGGTTG GGGACATGGT
6051 AAGAGGGTGA GCAGTAGCTG GGCTGCCGGG AATAAAAGTC ACACGTAAAA
6101 GGGGCTCTTG TGTCTAGACT CCCAATATCA GATTTGATCA CTAACCAGAA
6151 TTTTTCCTCC GGGTTTCCTA ATACCACACG GAGAAATCCT AACTTCCTAT
6201 GGGTCTACAG CTTTTTATAA AGAATCCTGT TATTTAGTCT ACTCATTTCA
6251 TTTGCAGTTT GAGAGAACGT CTGTGCTCTT TCTACGTCAA TGTTAACTTT
6301 GGGGCTGTGG TTAAGATGTA TATATTTTGT GTATGACCTG CAGGTAAAAC
6351 CACGGTGACC CAGTCAGTGG CAGATTCACT TAAGGCTGTC CTCTTAAAGT
6401 CACCACCCTC TTGCATTGGC CAGTGGAGGA AGATCTTTGA TGATGAACCA
6451 ACTATCATTA GAAGAGCTTT TTACTCTTTG GGCAATTATA TTGTGGCCTC
6501 CGAAATAGCT AAAGAATCTG CCAAATCTCC TGTGATTGTA GACAGGTAGG
6551 TATAAAGATG CCTTGAATTA GGCATTTTCT CCCTAATATA TAAGTGTGTG
6601 TGTGTGTGTG TGTGTGTGTG TGTATACGTA CATGTATATG CCAGGAAAAA
6651 AATTGTGTTT AAGTCAAACT GTTATTATGA TAATAATAGG AATTCTCCTT
6701 ATGAATTGTT AATTACCTAT ACCAGGCATG GCATTTGCTA GAGAATTACA
6751 TATATAATAC TAGTATCTGG AACTATAACT TGGGTAGGTG AATGTTACAT
6801 GTTATTCCCA GTTACTGAT GAGAACTATA GATCTCAGAA AGGTAAAATA
6851 ACTTGCCAAG GTAAGCTGGA AATAGCATAC CGGGGACATT AATGAGTCTA
6901 TACTTTCAGT CATTTATTTG TTCATTGGCT TATTCAACAA ATACTTACTG
6951 GACACCTCCT GTGTGCCAAA GACTAGTCTC AATTTAGAGG ATTCAATGAT
7001 AAACCAGTGT ATTAGTCCAT TTTCATGCTG CTGATAAAGA CATACCCGAG
7051 ATTCGGCAAT TTACAAAAGA GAGCAGTTTA ATGGACTTAC AGTTCCATGG
7101 GGCTGGGGAG GCCTCACAAT CATGGTGGAA GGTACAAAGC ATGTCTCACA
7151 TGCCGGCAGA CAAGAGTAGA GAGCATGTGC AGGGAAACTC CCCTTTTTAA
7201 AATCATCAGA CCTTGTGAGA CTTATTCACA ATCATGAGAA CAGCATGGTA
7251 AAGACCTGTC CCCATGATGC AATTACCTCC CACTGGGTCC TTCCCACAAC
7301 ACATGGGAAT TCAAGATGAG ATTTGGGTGG GGACACAGCC AAACCATATA
7351 ACTCCACTCC TGGCCTCTCC CAAATCTCAT GTCCTCACAT TTCAAAACCA
7401 ATCATGCCTT ACCAACAGTC CCACAACTCT TAACTCATTT CAGCATTAAC
7451 TCAAAAGTCC ACAGCCAAAG TCTCATCTGA GACAAGGTAA GTCTCTTCCA
7501 CCTATGAGCC TGTAAAATCA AAAGCAAGTT AGTTATTTCC TAGATACAGT
7551 GAGGCTACAG GCATTGGGTA AATACAGCCA TTACAAATGA GAGAAATTGA
7601 CCAAAACAAA GGGGCTACAG GCTCCATGCA AGTCTGAAAT TCAGCTGGGC
7651 AGTCAAATCT TAAAGCTCCA AAATTATCTC CTTTGACTCT ATTTCTCATG
7701 TCCAGATCAT GCTGATGCAA GAGGTGGGTC CTCATGGTCT TGGACAGCTC
7751 CATCCCTGTG GCTTTGCAGG GTATAGCCCC CCTCCTTGCT GCTTTCACAG
7801 GCTGGTGTTG TCTGCAGCTT TTCCAGGTGC ATGGTGCAAG CTGTCAGTGG
7851 ATCTACCATT CTGGGGTCTA GTGGACAGTG GCTCTCTTCA AACAGCTCCG
7901 CTAGGTAGTG CCCCAGTAGG GACTCTGTGT TGGGGCTCCA ACCCCACATT
```

FIG.3C

```
7951  TCCCTTCCAC ACTGCCCTAG CAGAGGTTCT CCATGAGAGC CCCACTCCTG
8001  TAGCAAACTT CTGCCTGGAC ATCCAGGCAT TTCCATACAT CCTCTGAAAT
8051  CTAGGCGGAG GTTCCCAAAC CTCCATTCTT GACTTCTGTG TACCTGTAGG
8101  CTCAACACCA CATGGAAGCT GCCGAGGCTT GGGGCTTTCC CCCTCTGAAT
8151  CAAGAGCCTG AGCTGTACCT TGGCCTCTTA CTCAAGGCTA GAGTGGCTGG
8201  GACACAGGGC ACCAAGTCTC TAGGCTGCAC AGAGCAGAGG GACCCTGGGT
8251  CCACAAAACC ATTTTTTTCC TTCTAAACCT CTGGGTCTGT GATGGGAGGG
8301  GCAGCAGCAG AGGTCTCTGA CATGCCCTCG AGACATTTTC CCCATTGTCT
8351  TGGTGATTAA CATTTGGCTT CTCATTGCTT ATGCAAACTT CTGCAGCCAG
8401  CTTGAATTTC TCCTCAGAAA ATGGGATTTT CTTTTCTGTC ACATTGTCAG
8451  GCTGCAAATC TTCCAAACTT TTATGCTCTG TTTCCATTTT AAAACCGAAT
8501  ACCTTTAACA GCATCCAAGT CACCTCTTGA ATGCTTTGCT GCTTAGAAAT
8551  TTCTTCCACC AGTTACCCTA AATTATTCTC TCAAGTTCAA AGTTCCACAA
8601  ATCTCTAGGG CAAGGGCTAA ATGCCGCCAG TCTCTTTGCT AAAGCATAAC
8651  AAGAGTTACC TTTGCTCCAG TTCTCACCAA GTTCCTCATT TCCATCTGAG
8701  ACCACCTCAG CCTGGATTTC ATTGTCCATA TCATTATCAG CATTTTGGTC
8751  AAAGCCATTG AACAAATCTC TAGGGAGTTC AACCTTTCCC ACATTTTCCT
8801  GTCTTCTTCT AAGCCCTCCA GACTGCTTCA ACCTCTGTCT ATTACCCAGT
8851  TCCAAAGTTG CTTCCACATT TTGGGTATC TTTTCAGCAG CACCCCACTT
8901  CTGGTACCAA TTTACTGTAC TGGTTCATTT TCACACTGCT GATAAAGACG
8951  TACACGAGAC TGGGCAATTT ACAAAAGAAA GAGGTTTAAT GGATTTACAG
9001  TTCCATGTCG CTGAGGAGGT CTCACAGTCA TGGTGGAAGT TACGGCACAT
9051  CTCACATGGC AGCAGACAAG AGTAGAGAGC TTGTGTAGGG AAACTCCCCT
9101  TTTTAAAACC ATCAGATCTT GTGAGACTTA GTCACTATCA TGAGAACAGC
9151  ATGGGAAAGA CCTGCCCCTG TGATTCAATT ACCTCCCACT GGGTCCCTCC
9201  AACAACATGT GGGAATTCAA GATGAGATTT GAGTGGGATC ACAGCCAAAC
9251  CATATCAATG AGATAGATAA GTCCCTATTT TCATGGAGCA AACTTAACAT
9301  TATAGGAGAA GAAAAGTATC AGGTGAACAA ATACATAAAA TAATACATAA
9351  GATGAGGTAA GATAATATCA AAGCATGATA AATGCAGGGA AGAGGAAAAA
9401  TCAAAGTAAT GTGCTAAAAA ACGGCTAACC CTCCACTAGA TATGGTTTAG
9451  GAAGGCCTGT CTGAGAAAGC ACCATTAGTC AGAGCCCTGA TTTAAAAAAA
9501  AAAAAGGCAA ATGTGAAAAT TCCCGGGTTA ACAGAAAGCA CTGTGGAGAA
9551  AGAAATCTGC AAGAATGAAG CTAAGACTGA AATAAGCTAA CATATCTGAC
9601  AACTAGAAAA TGTTATATGT TCTGAGAACA TAGTAGATGT GGAGGTGCTT
9651  TGTGGATGAA TGGGAAGAGG AAGGTTGGGG CAGGTCTGTA GGGCTTGTAG
9701  GCCATTCATA GAATGGATTT TATTCTGAGT GCACTGGGGA GCCATTGGAA
9751  TGTTTCTGAT AAAGGAGAGA CATAAACTGA TTTATACTTT AAAAATTCAC
9801  CTGTAAGAAA TAGCTTCACT TTGGGAGGCT GAGGTGGGCG GATCATGAGG
9851  TCAGGAGATC GAGACCATCC TGGCTAACAC GGTGAAACCC CGTCTCTACT
9901  AAAAATACAA AAAATTAGCC GGGCGAGGTG GTGGGCACTT GTAGTCCCAG
9951  CTACTCGGGA GGCTGAGGCA GGAGAATGGC ATGAACCCCA GGGGGTGGAG
10001 CCTGCAGTGA GCCGAGATCA TGCCACTGCA CTCCAGCCTG GGCGACAGCG
10051 AGACTCCGTC TCAAAAAAAA AAAAAAAGA AAAGAAAGA AATAGCTTTA
10101 GGTCAGGTGC AGTGGCTCAC ACCTGTAATC CAAGCACTTT GGAAGGCTGA
10151 GGTGGGAAGA GTGCTTGAGC CCAAGAGTTC AAGACCAGCC TTGATAACAT
10201 AGTGAGACCT TGTCTCTACA AAAAATATTT AAAAAAATAG CTGGGTATGG
10251 TGGCACCCAC TTGTAGTCCC AGCTACTTAG GAGACTCAGG AAGGAGAATC
10301 CCTTAAGCCC AGGAGGTCGA GGCTGCAATG ACAAAGCAAG AGGATGACAC
10351 AGCAAGAGGG GCCTTGTCTC AAAAAAAAAA AAAAAATCCC AAAAACAATA
10401 AAACAAAAAA CAAAAAAGAA GAAAAAAATA GCTTTAAAAA TACTATAAGA
10451 AAGAGGAAAG GATATGACAA GCAGGTCATA CTGAACTTAC ATCACGATGA
10501 CAAATGGATG AGAAGATTAT AGTCACCATG AGATTCCATT TTACTCCCAT
10551 CTGGATTTCA TTTTACTCCC CTCCAGTTGG TGAAACTACT ATAACTAAAG
```

FIG.3D

```
10601  GTTTCTTCAT ATGATATGGA TCAATAGAAA CTCTCATATG ATGCTAGTCA
10651  GAACATATCA TATGATAGTA GCATAATCAC TTAGAGAGCA GTTTGAAAAG
10701  ATGTAGCAAA GTGGAAGATT GCTCCTGCCT ACTGAAGAAA CACTCACAAA
10751  AGTTTCTTTC AGCTTCCTTC ATACTGTTGC AAAATTTGAA AAACCTAAAG
10801  CCCATCAACA GGAGAAAGCA TAAATAAATA CCAGCATATG TATAAGGTGG
10851  AAAACCATAC AGCAGCAGTG TAAATATGTT GTGCAATGCA TGAGGGCACA
10901  CACATTACAA AACCGTAATG TTGAATGAAA ATGTCAAGTT GCCAAAAGAT
10951  GTTTATTCAG TAGAATACAT GCAGTTATCC ATACTGCAAA GAGTAGAGAG
11001  ATGAAAGGAT GTTGAACAGC AGATTTAAGA AAGTTGTTCT CTGGGAAGTA
11051  GAGATAAATG TGGTTGATAA GGAGATCAGA AGGACTTTGA TTGTGATTGG
11101  ATTATTTCTT AACATTTCTT GAATGTTCAT TTTCTCCAAA GATTTACTTA
11151  TTTTTGTAAA CATAAGCAAT TGCATTTAAG TATGGCATAG TTGGTAAAGA
11201  ACATTAATCA TAAATGTAAA TCTCAAGGAA TTTCAAGAAG TGAACACAGT
11251  CAAGTCACCT GTACCCAGAT CAAGAATGAG AGCCTGCCAC AGCCCCTACA
11301  CCCCTGTTCT GCCCCCACCC AGTCACTGCC CATTTCCTCC CCAGGGGTAG
11351  CAACTGTCCC AACTGCCATA GCCATATATT AGTTCTGCCT GTTCTTAAAC
11401  TGCCTACAGA TGCAACTATT TGTTAGGTAT GGAGTTTTAT TTGCACCTGA
11451  CTTCTTTCAT ACCACATGTG TTTTGAAGAT TTGCCTGTGT TGTTGTGAAC
11501  TAAATTTTAT GCATTTTTGG TGCACATATG GATGCAGTTC TGTTACATAG
11551  GTTCCCAGGA GCAGAACTGC AGGGGCATGG GGTTTGTGGC TGTTCAGGTT
11601  TGGTAGATGT TGCAAAAAGT ATTCTAAAGA GGTTGAAAGA ATGTTGAGTC
11651  TCCTCCCCTC CCCACAGCAG TATTTGCCAA TTCCCTGTGA CTAACAGCCC
11701  TGTTGACATT AGTATTACCA GGCTTTAATT TTGACTCCTC TAGTTTTTCC
11751  ACTTGTTCCT GGTGGGTAAG CTGGTCACTG AAAAGCTGAT TTGTCCTATC
11801  TGGACACAGA ACTACTACTC CTTTCTTGAA AGTATATCTT TTTCTGTACA
11851  CTTTTCTGTA TGTCTGAAAT ATTCCATCAA GAGACCACCC TGACTGTATG
11901  TGGAGAATAA AGTGTGTGGT GGGGGAGGGG CAAGAAAGGA AAAAGAATCA
11951  GCTAGAAGGC TGTGGCTGCA GTCTAGGCTG TGATGGCCCT TGAGTAGTTT
12001  TAATCCTGGG ATGACAATAG GGATGGCAAT GGGGATAACA ATAATAATTT
12051  CAAGGTTGGC AAGTTACATG GAATCTTAGG ATGAACTGAG AAGGATACGA
12101  AATCTTGTTC CTTTATGGGA AGGCTTTGCC TGGAAAATGT TTTTGCCCTA
12151  TTGTTAACAT GCCCGATGTT ATCATATGTG ATATCTGTAT TAGTTCTTTC
12201  TCACACTGCT ATAAAGACGT ACCTGATACT GGGTAATCTA TAAAGAAAAG
12251  AGGTTTAGTT GACTGACAAT TCTGCATGGC TATACGGGAG GCATGGCTGG
12301  GGAGGCCTCA GGAAACTTGC AATCATGGTG GAAATTGAAG AGGAAACAAT
12351  GGCAACAGGA GAGAGAGAGA GAGAGGCAGG GGCAGGGGCA GGGGCAGAGG
12401  CGAGAGAGCA GGGGGAAGTG CTACACATTT TAAACACCCA GATCTCATGA
12451  CAACTCACCA TCACGAGAAC AGCAAGGGGG GTGTCTGCCC CCATGATCCA
12501  ATCAACTCCC ACAGGCCTC ATCTCCAACA ATGGGAATTA TTAGGTTGGT
12551  GCAAAAGTCA TTGTGGTTTT TGATATTATT ATTAATGGCA AAAACCGCAA
12601  TGACTTTTGC ACCAACCTAA TACCCTTTGG CATGAGATTT TGGTGGGGAC
12651  AAAGAACCAA ACCATATTGA CATCTTTTTT GATACAGTCC CCTTTATTTC
12701  CAAGAGAAAG ACTAAGGTTT TCCTAGTAGG GTATGACTTT CGAGGTCCAT
12751  TATGTCCTAG GATGCCTGCG GATCCTGAAG CAGCACTGGC CACTGTGTGC
12801  AGGCAGGGAT TTCTGCACTC TGTCCCCCAG TTTTCTGATC TGTTAAGTGG
12851  GGATACTCAT GCCCCCTTCC CTGCCTACTG TCAAGAGTTG TGATGATGAT
12901  TCAGTGAGTG GATGTGTGTG GAAGTACCCT GAAAATAGGA AATTGCTATT
12951  AAAATATAAA GCATTATTAT ATGAGCAGTG TATAATGTGT TGGCAAATTG
13001  CTTTTGATTT GAACTAATGT GGCTTCCCTG ATAGCAGGAG TGGAGAATAC
13051  TAAATAGTGG GAAGCATCTG AAATTGATGG GCTAAGGGTG CAATTATTTA
13101  AAACAAGCAG CCGTATTTTC AATGGGAGAA CTCTATAGGA AACAGGTCCT
13151  TAATTCTTCC CTTGATTTGT CTTCTTTGTG TGTGTGAATT GCCTGCAATT
13201  TAGTTCTTTA AAGAAATGCT GTATCACCTT GTCAGATGAA AAGAAAAGAG
```

FIG.3E

```
13251 CAGTTATTTG TTGTCTTTGT GGATTTTATT CATGTTTAAA GATTTTAATA
13301 AAATCCATTT TAGACAGTAC CATTATCTAG CTGAAAAATA TGAGAGACAG
13351 TAATTTTTAA CGGGGACTGT GGTTAAGGTT GGAGTCTTAA TCACCCCATT
13401 ACCTTTAAAA ATCTATTCTT GCTGGTGATT TTTCTACAAT AAAGAAGACT
13451 TTAAAAATAA GATAATATCA GACTCTATAT TCATAGGTAG GTATTTAATT
13501 CAATGAATCT GGAGCATGTG CTGACCATGG TGTAAATTAT AGTTTAAGTA
13551 CCAGAAAAAG AAAACTGAGA CCCTAATTGG CTTTTTTTGA GCTTGAGGGA
13601 CAAAATTCAT CTGGCAGAGA GAGTGAAAGT ACAAGTTTGT GAGTAACAGG
13651 AGTTGGGTAA GTAACACATA GGAAGGTGTC CAGGCAGAAT TCACAGGAGC
13701 TGGCAGTGGC CTGAAGCTCT CAGAGCACAC TTTTGGAGGT GAACAAGGGC
13751 TTTGAAGGAT GGATGGTGTT GAGATTATCA ACTCCCAAGT GAATTTTTCT
13801 TTTTTTTTTT TAGATGAAGT CTCGCTCTGT TGCCCAGGCT GGAGTGCAGT
13851 GGCGCGATCT CGGCACACTG CAAGCTCTGC CTTCCGGGTT CACGCCATTC
13901 TCCTGCCTCA GCCTCCCGAG TAGCTGGGAC TACAGGTGCC CGCCACCACG
13951 CCCGGCTAAT TTTTTGTATA TTTAGTAAAG ACGGGGTTTC ACCATGTTAG
14001 CCAGGATGGT CTCGATCTCC TGACCTCGTG ATCCACCCAC CTCAGCCTCC
14051 CAACCAAGTG AATTTTTTAC TTGTGTCCTT TTCAGTGCTG TCCTGTGTTC
14101 TGTTATCATA ATTTGCAATG ATCCGGCTTT AGTTATAACC AGTGTCTGAT
14151 AAGAATTAGA TATTTATCTT ATAGTAACAG TGTGATACAG TTTTTTTTAA
14201 GCACTTGTCT GTATTTGTAA CAACTATGGA AGGAAAACAA ACCTTGCATG
14251 ATCTGTGTTT TCCAGATGAG GAGATGGAGG CTATATTAGC TTAGATGACT
14301 TTTACCTACA TGTACAAAAC AGGTGGGGCG GGGGACACAG GCAGAATAAT
14351 GTACAGTTCA GGTAACACAG GGAATTTATT ATGTGGATAC CACTGTGTAC
14401 TTTTCACTGT GGAGAGGAGT TCAATTCTAA AATGATCAAA ATTTTAGGAT
14451 TTTAAAGAAT TGGGCCGGGC ATGGTACCTC ACGCCTGTAA TTCCAGCACT
14501 TTGAGAGGCC AAGGCGGGTG GATCACCTGA GGTCAGGAGT TTGAGACCAG
14551 CCTGGCCAAC ATGATGAAAC CCCATCTCTA TTAAAAATAC AAAAATTAGC
14601 CGGGCGTGGT GGTGCATGCC TGTAATCCCA GCTACTTGGG AGGGTGGGGC
14651 AGGAGAAATG CTTGAACCTG GGAAGCAAAG GTTGCAGTGA GCTGAGATCG
14701 TGCCACTGCA CTCCAGCCTG GGCAACAGAG TGAGACTCCA CCTCAAAACA
14751 AAAATAAAGG ATTGAAGGTG GTAATTTGAA AGTACAAATG AGGAGGGGCC
14801 CCTGGGTATC TCTACGTTGG AATGTTTATA TCATAAATAT TTATTGTGAG
14851 TGATGGTCCT TTTATATTGG ATCTGAATTG TCCATTTAGT CCTTTAAAAT
14901 TGGAAGATGG CATGAACAGG GCAAGAGTAT AATAAACTAT GCTGATAAAT
14951 GAAATCGTTC TAATTCATTT ATTCATTTAT ACACCCAAAT AACATTCTTT
15001 CATTGCATAT CTATTATGTG CCAGACATGC ATTACTAAAA AAGATTTCCC
15051 ACTCAAGAAA TTACCTAATG GAGGAGACAA TAGATATTAC ACTTATAACA
15101 AGTAGTTCTG ATTTGCAATG AGGAGTTTTT CAGTAGAGTC ACGTAGAAAG
15151 GGTTTTGAGA GCACAGAGGA GAAAACAGTC AATTCTGTTT GGGGGCTTCC
15201 TAGGAGTCTG AAGGGAGAGG AGAGTTTTGC TGGCTGAGAA CCTCACTCTC
15251 ACCAGAGGAA AAGGTAAGCA GGTGCAGACT AGGAGGGATG TTCTGTGTCT
15301 TACCAGAAGA CCAAGCATTT CCTGTAGGTT GTAGGAAGCC ACTAGGCATT
15351 TTTAAATAGA GACTGATTTG ACTTTTGTGT ATGGTAATAA CTTTGTTTTC
15401 CTCCCCCAAA ATCACTTTTT AAAACAGCCA GCAGAAGGAG CGACTGACTT
15451 GCTTAGGGAG GACTTTCATG GAGCTGGGCA GGGCATATTT GTCTCCCTGT
15501 CTCATACTGA GGCACCATCA GCAGACTGGA TAGTTGGGAG AAACAAAGAG
15551 GCTTCTACCT CAGGGGTCCC AGAATGTGAA TTTCATTGGC AAGTTCAAGT
15601 GAAAACAGTG TAGGAACTGA CATGGCCTTT CCAGGATTTT AGTCTGCCAA
15651 GACACAGCCC TTAAATACAA ATGAACTGCC AAACAGGTTC ATTGTCCCCT
15701 GTCACCCTCC ATTCTTTCAT AGAGGAATGC GGACAGCAGG ACCAAAAGA
15751 TGTGATGACA GAGGGGAGGC CACACTAAAT GGTAGTTTGA GATGGGTCAA
15801 TGGAGCTGTG TGAAGAACAC ACTGCATTAT TACTGTTGTC AATTTTATTT
15851 TTTAAACAAT ATTGTATAAC TTTTTTTAGT TTATAAAATT TAATTTTATT
```

FIG.3F

```
15901 TAACTTATGC AATACTAGAA AAACTTCTGT AGAGCCAACC CTGGTTTCAT
15951 CATTCCTGGC TGCTGATTTT CAGATGCTAC TTTGACTTCT TCTGCAGACA
16001 GAGAACTCAC TACCCCATTC CTTCTCAGGT ACTGGCACAG CACGGCCACC
16051 TATGCCATAG CCACTGAGGT GAGTGGGGGT CTCCAGCACC TGCCCCCAGC
16101 CCATCACCCT GTGTACCAGT GGCCAGAGGA CCTGCTCAAA CCTGACCTTA
16151 TCCTGCTGCT CACTGTGAGT CCTGAGGAGA GGTTGCAGAG GCTGCAGGGC
16201 CGGGGCATGG AGAAGACCAG GGAAGAAGCA GAACTTGAGG CCAACAGTGT
16251 GTTTCGTCAA AAGTAGGTGT CCCAGTGCAA TGCAATGTGA GCGGCAGGCA
16301 TTCCTGAAGG GAGATGAACC ACTGGCACTG GCTTTAGGAT TGTGAGGAAG
16351 TGATATTGTT TCCAGTTTTC AAACACAAGA GACAACATCC TCTAAGTTAC
16401 TTCAGCCCCT TCCAATGGGC TTGTCACCAC AGGGCTGCAG CATTGTTATC
16451 TTAAAGCAAA GGTCATCGGA CTAGGGATCA GACCCTGCCA CTGATCCTGG
16501 CTGTGCTAGG AGCAGCTGCA CCTGGGTAAG ACAGTAAGTG TCTCTGTGCC
16551 TCAGTTTCCC CAGTCATAGT ATAATCACAC AGAGCACTAG ATAACGAGCT
16601 CATAGTAACA TCTACCTATT AGATGCTTCC CGTGTGTCAG GCATTTTACT
16651 GATGTTATGT CATCCTTGTG AGGAAAACAT TAGCCGTATT TTACAGTTTA
16701 CAACTTTAAG GCTCAAAGGA TTAAGTGATT TGTCTAAATG TACATAACTA
16751 TTCACTAGTA AAACCGGGAT TAAAATCTTT CTGATTTTGC AGCCAGTGTT
16801 TTTGTTTTAA TTAGAAAGTT ATAAACACGA CTGCAGAAGA GAGTCTGGCC
16851 AGGCCTCCTG CCTCATGACT GAGTATGAAT CAGTTCTACA CCACTGCCTT
16901 TAAAAACTGA AGCAGAAATA TTTTCTCTAA CTGAACAATG ATAGCCCTGT
16951 TATCATAACA TAGTAATGTT ATAAATAATG GTAGCTGCTG TGGGTAAAGA
17001 TATTATGTTA AGCAATTTAC TTGTATTAAT TCCATTAAAC TTCAGTGAAC
17051 ATTTGCAAGG AAGGTACGGT TTCAGTCTTC ATTTTGCAGA ACAGGAAACT
17101 GAGACACAGA GAGGAGAAGA GATTTGACCA ATTCACTTGG CTAGGAAGTG
17151 GTCAGGCAGA GTTGTGAATG CAGACGATCC ACCTCGACAC CCCTATTTTA
17201 ACCACAGTGC TATAAGGATT CCATAAAGAA ACAGGCACTA GTCACTCTGT
17251 ATACACATGA AGGCTAGCTA GCATGGAAAG GATATGTAGA TTTCTGGCAA
17301 AATATTAGAA GAGTCCCATG CATATATTAA GGACTGTGGC TTGTATGAAA
17351 ATTATTCAGG GCACAGACTT GGGGGAAATT TGCCACTGAA CAAATTACCT
17401 AAATTCTTTG AGCTTCAGTT GCCTTCTCTG CAAAACAGGG ATGACAATAG
17451 TCTTCCCTCC TAAGGTTACT TTGAGAATTA AATGAGAAAA ATCATGCAAA
17501 ATGCTAATGC TTGGCAGAAA ACAGGTATTC AACAAGTGCT AGCTATTAAA
17551 CATTATTATT CATTTATTAT TTGTTAAACA AAATGCATGA ACGTCTTCTG
17601 TGGGCAAAGC TAGTTACAGT GAGATAAATG ACATGGGAAG CTTGCTTCAA
17651 GCTATTTATA CTATGGTAGG AAAAGAACAT TAATGCAAAT AGCTGTGTGA
17701 AAAAGTAGAC CAACTCTTTG TGTTTTGCCT GTCCCCAGGG TAGAAATGTC
17751 CTACCAGCGG ATGGAGAATC CTGGCTGCCA TGTGGTTGAT GCCAGCCCCT
17801 CCAGAGAAAA GGTCCTGCAG ACGGTATTAA GCCTAATCCA GAATAGTTTT
17851 AGTGAACCGT AGTTACTCTG GCCAGGTGCC ACGTCTAACT AGATTAGATG
17901 TTGTTTGAAA CATCTACATC CACCATTTGT TATGCAGTGT TCCCAAATTT
17951 CTGTTCTACA AGCATGTTGT GTGGCAGAAA ACTGGAGACC AGGCATCTTA
18001 ATTTTACTTC AGCCATCGTA CCCTCTTTCT GACTGATGGA CCCGTCATCA
18051 CAAAGGTCCC TCTCATCATG TTCCAGTGAG AGGCCAGCGA TTGCTTTCTT
18101 CCTGGCATAG TAAACATTTT CTTGGAACAT ATGTTTCACT TAATCACTAC
18151 CAAATATCTG GAAGACCTGT CTTACTCAGA CAGCACCAGG TGTACAGAAG
18201 CAGCAGACAA GATCTTCCAG ATCAGCAGGG AGACCCCGGA GCCTCTGCTT
18251 CTCCTACACT GGCATGCTGA TGAGATCGTG ACATGCCCAC ATTGGCTTCT
18301 TCCACATCTG GTTGCACTCG TCATGATGGG CTCGCTGCAT CTCCCTCAGT
18351 CCCAAATTCT AGAGCCAAGT GTTCCTGCAG AGGCTGTCTA TGTGTCCTGG
18401 CTGCCCAAGG ACACTCCTGC AGAGCCATTT TTGGGTAAGG AACACTTACA
18451 AAGAAGGCAT TGATCTTGTG TCTGAGGCTC AGAGCCCTTT TGATAGGCTT
18501 CTGAGTCATA TATAAAGACA TTCAAGCCAA GATGCTCCAA CTGCAAATAT
```

FIG.3G

```
18551 ACCAACCTTC TCTGAATTAT ATTTTGCTTA TTTATATTTC TTTTCTTTTT
18601 TTCTAAAGTA TGGCTCTGAA TAGAATGCAC ATTTTCCATT GAACTGGATG
18651 CATTTCATTT AGCCAATCCA GTAATTTATT TATATTAATC TATACATAAT
18701 ATGTTTCCTC AGCATAGGAG CTATGATTCA TTAATTAAAA GTGGAGTCAA
18751 AACGCTAAAT GCAATGTTTG TTGTGTATTT TCATTACACA AACTTAATTT
18801 GTCTTGTTAA ATAAGTACAG TGGATCTTGG AGTGGGATTT CTTGGTAAAT
18851 TATCTTGCAC TTGAATGTCT CATGATTACA TATGAAATCG CTTTGACATA
18901 TCTTTAGACA GAAAAAAGTA GCTGAGTGAG GGGGAAATTA TAGAGCTGTG
18951 TGACTTTAGG GAGTAGGTTG AACCAGGTGA TTACCTAAAA TTCCTTCCAG
19001 TTCAAAGGCA GATAAATCTG TAAATTATTT TATCCTATCT ACCATTTCTT
19051 AAGAAGACAT TACTCCAAAA TAATTAAATT TAAGGCTTTA TCAGGTCTGC
19101 ATATAGAATC TTAAATTCTA ATAAAGTTTC ATGTTAATGT CATAGGATTT
19151 TTAAAAGAGC TATAGGTAAT TTCTGTATAA TATGTGTATA TTAAAATGTA
19201 ATTGATTTCA GTTGAAAGTA TTTTAAAGCT GATAAATAGC ATTAGGGTTC
19251 TTTGCAATGT GGTATCTAGC TGTATTATTG GTTTTATTTA CTTTAAACAT
19301 TTTGAAAAGC TTATACTGGC AGCCTAGAAA AACAAACAAT TAATGTATCT
19351 TTATGTCCCT GGCACATGAA TAAACTTTGC TGTGGTTTAC TAATCTATGC
19401 TGTCATCCTG GGTACATATT GATTTGTCTG AAAAGTGCTT TCTCAGATTC
19451 CCCTTTTAAT ATTGTGATGT AAAGGAGGGA AATTTTGGTA AAGGAAGTTG
19501 AAAGGTGTGA GCTGGCAGGC TAAGTGGAAT TTGTGGTCAG AGTGCTTTCA
19551 GAGAAAGGGG AGGGCTATTG TTTTATTTTA CATATCATTT CCTCATTACA
19601 AATATTAAAG ACATTTTGTA ATTCATTCTT TTTACACCTG GACTTTTTAT
19651 ATACTGATAG GTATATATGA CTTACGAGTA TTTTGTAAAA TAGCACCTCC
19701 TACCCTAAAA CTGATGGCAA GTAACCCTTT GCTTGGCTCT GCTCATTGCA
19751 AGACGAGCTT TGGTTTTGTT CCTGTGATAG ACCATTAGTT ACCCCAAAAT
19801 TTATTCTTCC TTTCTTCCAT GGTAATGTAA TATTTAGCTT GGTACATGGG
19851 TGCCAATAAT TCCTAGTGCA TTTCCAAGGC TCCCTTAACA GCTGGAGGTG
19901 GGCGACTGGC TAGTTTCTTG CCAATAGTAT GTGAGCAGAA GGAATACCTG
19951 AAATGTCAAG GGGATATTAT CACTTTCCCC TTTAACTCTT CATATCGGCT
20001 GTATTCAGAG GTGATAGCCA TCTAAGGACC AAGAGATGAG GATGACACTA
20051 AAAGGAATTA GCTTGCCTTA GGTAAATAGC AAGGGAAGGG TCCCCAGAGA
20101 GCCCTCGGCC CACCAGTCAG TGCCTCACCC CACATAATGT AAAAAGCAGC
20151 CTGGGGAAAA AATCAAGCTG CAGGCACTGA TAAGGGAACT AGCACAGGGT
20201 GTTGTGCCTG GAGACATGCC TACGGCTGCA CAGATAGGAG AGCCTCTGGC
20251 CCATTCAGAT AAAAGCTTGC ACAAACCTCT GGCTCACTCA GATGAGGGAA
20301 CAAGTCCTGG CATAAAAACA CCTTTGTCCT TTGTATAGTC AGCAGGCTCC
20351 CAGGAAAAAG TTTTTTTCTC CTTTTGTGGG CGTGGGCACA GTGGGCTCCA
20401 GTTAGTTCCA GTGGGCACTT TCCTTGCCAG TTTTTGGACT GTGAGTCTGG
20451 CCTCTGTGAA TCATAACTTC AGCCCCTGAT TGGTCCCAGG CAAAGGTCCT
20501 AGGCCAGGCT TTCTGATTGG TCCTGGGCCA GGGTGCCTGG CCAAGCTGAG
20551 TCATGCCTTC TCCAAGACAG CCGGTAGACT AAGCACATTC ATTCCCCTTT
20601 CCAGCCCGTA AAACCCCCAC AACTGGCCTC ATAGTGGGCA CCCCATTAGA
20651 GCTCCCCCTT CTGCTGGCAG AGAGCTTTCT TTTTTCGCTT ATTAAAGTTT
20701 CACTCCAACT TCACCCTTGT TGTCTGCACT CCTTAATCTT CTTGGAATTA
20751 GGACAAAGAA CTCTGGATAT TATCTCAGAC AACGGGAGAC TGTTACATCT
20801 TGGTGCATTG GTAAGATTAC AACACATTTT GGTGCATTGG CTGGGAAGAA
20851 GGGAATTCAT CAGAAGGATG ATTAAGAGTT GACCTTTAAC TTTCACCTTT
20901 ACTTGCATTT CTGAGGCTTC TTGTCTATTC CAGTCTAGTT TGCTTTCACA
20951 GAGGGCCTAG CCATCA
```
(SEQ ID NO: 3)
FEATURES:
Start: 2032
Exon: 2032-2706

```
Exon:    4151-4265
Exon:    6344-6545
Exon:    16029-16262
Exon:    17739-17859
Stop:    17860
```

Sim4 results:

```
Exon:    2001-2706,  (Transcript Position: 1-706)
Exon:    4151-4265,  (Transcript Position: 707-821)
Exon:    6344-6545,  (Transcript Position: 822-1023)
Exon:    16029-16262, (Transcript Position: 1024-1257)
Exon:    17739-18966, (Transcript Position: 1258-2491)
```

SNPs:

| DNA Position | Major | Minor | Domain | Protein Position | Major | Minor |
|---|---|---|---|---|---|---|
| 4530 | G | C | Intron | | | |
| 5856 | C | T | Intron | | | |
| 6594 | - | G | Intron | | | |
| 10987 | C | T | Intron | | | |

Context:

DNA Position

4530

TCCAGGTTGTTGCCATCGAAGGACTGGATGCCACGGGTAAGATAATATTACCTTTTAGTT

ATAGGCAATGACACTAACTGATTAGTTGCAGAAACAGAAATACTTCCTGCAAAACCAAAC

TTTATATGGAGCCTTATGTGTGCCCCTACTGTGTGGCAGGCCCTGTGCTAGGCAGGCCCT

GGGATGCAGAGATGAATAAGACCTTCAATATGAAGCAGCATGATGTGTGGGCGCGGATCC

TCAGTGCTCTGGCGGAACACAGGAAGGGCACTGAATCTGGCCTCTGTGGGGCTTTGTCGG
        [G,C]

TGGAGTGCATGGTCAAGGGTGATACCTGGATTGTATTTTAAGTACAGATAGGAGTTGGTC

AGGTGATGAAAGCAGGTAACATCCTCCAGACAGAAGAAATAGCCTGGGCAAAGGTGCAGG

GGCTTGAACCAGGGTGGTGTGTCCAGGAACCACAGGCAATTCAGAGATTCTTCTGGAGCA

AAATGTGGAAGAACTAGGAAATGGAAGAAAAAAAGCCTTCTGAGCTGTCAAACTGAGGT

CAAAATATAATGTGTGCTCACATGAGACCAAAGTACAAAAGGGGCAGACATGCTGCTCCT

FIG.31

5856
AGAAAATAGATAGTTGGCAATAAAGTGTTAAGTGTGTGATAGAGAAACTTAAAAATAAAT

CGAAACAGTAGGAGCTCAGAGAAACTAGTGCACAGTGTGCTGGAGTAGATCTTCTCATCA

CCACCTGTCCTGAGCTCCAGGCAGCAGCTGAGAATTGTGAGATGGGCTCTGGGAAGGGAC

TAATCTGTCACCCGAGGCTGTGCAAGGGGGAGTCAGAAAGTCAATGAGGCCTAAGCAGTG

CCTTTGAGGAGAAAGCTGAAGCCTAAAGCAGATACAAAAGCTCTAAAGGCCAAGGCCAAG
[C,T]

CCAAAGGGGCAAGCACAGGAGTGAGTGGTAGAACCAGGGCTGGAAATTGGAAAGGGATTG

CACAGAAGTGGAAGCAGGGTATGAAGAAGGTAGAAAGAGAGGAGGGGCGAGAAGAGTTGC

TGTGGATGCCAGGTGTGGGTTCATCAACTATAGACAATAAGAGGAGAGAAAGTCTTCTGG

GTTGGGGACATGGTAAGAGGGTGAGCAGTAGCTGGGCTGCCGGGAATAAAAGTCACACGT

AAAAGGGGCTCTTGTGTCTAGACTCCCAATATCAGATTTGATCACTAACCAGAATTTTTC

6594
TAACTTTGGGGCTGTGGTTAAGATGTATATATTTTGTGTATGACCTGCAGGTAAAACCAC

GGTGACCCAGTCAGTGGCAGATTCACTTAAGGCTGTCCTCTTAAAGTCACCACCCTCTTG

CATTGGCCAGTGGAGGAAGATCTTTGATGATGAACCAACTATCATTAGAAGAGCTTTTTA

CTCTTTGGGCAATTATATTGTGGCCTCCGAAATAGCTAAAGAATCTGCCAAATCTCCTGT

GATTGTAGACAGGTAGGTATAAAGATGCCTTGAATTAGGCATTTTCTCCCTAATATATAA
[-,G]

TGTGTGTGTGTGTGTGTGTGTGTGTGTATACGTACATGTATATGCCAGGAAAAAAATT

GTGTTTAAGTCAAACTGTTATTATGATAATAATAGGAATTCTCCTTATGAATTGTTAATT

ACCTATACCAGGCATGGCATTTGCTAGAGAATTACATATATAATACTAGTATCTGGAACT

ATAACTTGGGTAGGTGAATGTTACATGTTATTCCCAGTTTACTGATGAGAACTATAGATC

TCAGAAAGGTAAAATAACTTGCCAAGGTAAGCTGGAAATAGCATACCGGGGACATTAATG

10987
AGCAGTTTGAAAAGATGTAGCAAAGTGGAAGATTGCTCCTGCCTACTGAAGAAACACTCA

CAAAAGTTTCTTTCAGCTTCCTTCATACTGTTGCAAAATTTGAAAAACCTAAAGCCCATC

AACAGGAGAAAGCATAAATAAATACCAGCATATGTATAAGGTGGAAAACCATACAGCAGC

AGTGTAAATATGTTGTGCAATGCATGAGGGCACACACATTACAAAACCGTAATGTTGAAT

FIG.3J

GAAAATGTCAAGTTGCCAAAAGATGTTTATTCAGTAGAATACATGCAGTTATCCATACTG
[C,T]
AAAGAGTAGAGAGATGAAAGGATGTTGAACAGCAGATTTAAGAAAGTTGTTCTCTGGGAA

GTAGAGATAAATGTGGTTGATAAGGAGATCAGAAGGACTTTGATTGTGATTGGATTATTT

CTTAACATTTCTTGAATGTTCATTTTCTCCAAAGATTTACTTATTTTTGTAAACATAAGC

AATTGCATTTAAGTATGGCATAGTTGGTAAAGAACATTAATCATAAATGTAAATCTCAAG

GAATTTCAAGAAGTGAACACAGTCAAGTCACCTGTACCCAGATCAAGAATGAGAGCCTGC

Chromosome Map: chromosome 2

FIG.3K

ISOLATED HUMAN KINASE PROTEINS, NUCLEIC ACID MOLECULES ENCODING HUMAN KINASE PROTEINS, AND USES THEREOF

FIELD OF THE INVENTION

The present invention is in the field of kinase proteins that are related to the thymidylate kinase subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Protein Kinases

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure, which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, G. and Hanks, S. (1995) *The Protein Kinase Facts Books,* Vol I:7–20 Academic Press, San Diego, Calif.).

The second messenger dependent protein kinases primarily mediate the effects of second messengers such as cyclic AMP (cAMP), cyclic GMP, inositol triphosphate, phosphatidylinositol, 3,4,5-triphosphate, cyclic-ADPribose, arachidonic acid, diacylglycerol and calcium-calmodulin. The cyclic-AMP dependent protein kinases (PKA) are important members of the STK family. Cyclic-AMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including cancer, thyroid disorders, diabetes, atherosclerosis, and cardiovascular disease (Isselbacher, K. J. et al. (1994) *Harrison's Principles of Internal Medicine,* McGraw-Hill, New York, N.Y., pp. 416–431, 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases. CaM-kinases are involved in regulation of smooth muscle contraction (MLC kinase), glycogen breakdown (phosphorylase kinase), and neurotransmission (CaM kinase I and CaM kinase II). CaM kinase I phosphorylates a variety of substrates including the neurotransmitter related proteins synapsin I and II, the gene transcription regulator, CREB, and the cystic fibrosis conductance regulator protein, CFTR (Haribabu, B. et al. (1995) *EMBO Journal* 14:3679–86). CaM II kinase also phosphorylates synapsin at different sites, and controls the synthesis of catecholamines in the brain through phosphorylation and activation of tyrosine hydroxylase. Many of the CaM kinases are activated by phosphorylation in addition to binding to CaM. The kinase may autophosphorylate itself, or be phosphorylated by another kinase as part of a "kinase cascade".

Another ligand-activated protein kinase is 5'-AMP-activated protein kinase (AMPK) (Gao, G. et al. (1996) *J. Biol Chem.* 15:8675–81). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected. This distribution suggests that its role may extend beyond regulation of lipid metabolism alone.

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) *Nature* 365:781–783). MAP kinase signaling pathways are present in mammalian cells as well as in yeast. The extracellular stimuli that activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin-1 (IL-1).

PRK (proliferation-related kinase) is a serum/cytokine inducible STK that is involved in regulation of the cell cycle and cell proliferation in human megakaroytic cells (Li, B. et al. (1996) *J. Biol. Chem.* 271:19402–8). PRK is related to the polo (derived from humans polo gene) family of STKs implicated in cell division. PRK is downregulated in lung tumor tissue and may be a proto-oncogene whose deregulated expression in normal tissue leads to oncogenic transformation. Altered MAP kinase expression is implicated in a variety of disease conditions including cancer, inflammation, immune disorders, and disorders affecting growth and development.

The cyclin-dependent protein kinases (CDKs) are another group of STKs that control the progression of cells through the cell cycle. Cyclins are small regulatory proteins that act by binding to and activating CDKs that then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

Protein tyrosine kinases, PTKs, specifically phosphorylate tyrosine residues on their target proteins and may be divided into transmembrane, receptor PTKs and nontransmembrane, non-receptor PTKs. Transmembrane protein-tyrosine kinases are receptors for most growth factors. Binding of growth factor to the receptor activates the transfer of a phosphate group from ATP to selected tyrosine side chains of the receptor and other specific proteins. Growth factors (GF) associated with receptor PTKs include; epidermal GF, platelet-derived GF, fibroblast GF, hepatocyte GF, insulin and insulin-like GFs, nerve GF, vascular endothelial GF, and macrophage colony stimulating factor.

Non-receptor PTKs lack transmembrane regions and, instead, form complexes with the intracellular regions of cell surface receptors. Such receptors that function through non-receptor PTKs include those for cytokines, hormones (growth hormone and prolactin) and antigen-specific receptors on T and B lymphocytes.

Many of these PTKs were first identified as the products of mutant oncogenes in cancer cells where their activation was no longer subject to normal cellular controls. In fact, about one third of the known oncogenes encode PTKs, and it is well known that cellular transformation (oncogenes is) is often accompanied by increased tyrosine phosphorylation activity (Carbonneau H and Tonks NK (1992) *Annu. Rev. Cell. Biol.* 8:463–93). Regulation of PTK activity may therefore be an important strategy in controlling some types of cancer.

The present invention has a substantial similarity to murine thymidylate kinase. A clone of 3.3-kb cDNA, also designated as TYKi, that is a member of the thymidylate kinase family of genes was discovered by stimulating with LPS. LPS, a bacterial endotoxin, induces the expression of many genes in macrophages. This clone was obtained by screening a cDNA library prepared from RNA isolated from the murine cell line RAW264.7 after bacterial LPS treatment. TYKi is quite similar to all thymidylate kinases for which there are sequence data. It conserves two very important domains in these kinases, namely, the catalytic domain or P-loop and the nucleotide binding domain. After LPS exposure, the TYKi message appears at 2 h, peaks at 6 h, and declines at 8 h. LPS induction of TYKi is dependent on de novo protein synthesis. Increasing cytosolic cAMP with forskolin attenuates the LPS induction of TYKi. However, treatment with 8-(4-chlorophenylthio)-cAMP (CPT-cAMP) or dibutyryl-cAMP did not affect the LPS induction of TYKi. In contrast, activation of protein kinase C with phorbol ester augmented the LPS response, whereas inhibiting protein kinase C with 1-(5-isoquinolinylsulfonyl)-2-methylpiperazine (H7) suppressed the LPS response. Removing extracellular Ca2+ with EGTA inhibited LPS induction of TYKi, whereas increasing intracellular calcium with the calcium ionophore A23187 had little effect on the levels of the TYKi transcript. Inhibiting tyrosine kinase with genistein suppressed the induction of TYKi by LPS. For a review related to thymidylate kinase, see Lee J Immunol Jun. 1, 1995;154(11):6094–102.

Kinase proteins, particularly members of the thymidylate kinase subfamily, are a major target for drug action and development. Accordingly, it is valuable to the field of pharmaceutical development to identify and characterize previously unknown members of this subfamily of kinase proteins. The present invention advances the state of the art by providing previously unidentified human kinase proteins that have homology to members of the thymidylate kinase subfamily.

SUMMARY OF THE INVENTION

The present invention is based in part on the identification of amino acid sequences of human kinase peptides and proteins that are related to the thymidylate kinase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate kinase activity in cells and tissues that express the kinase. Experimental data as provided in FIG. 1 indicates expression in the tissues showed in FIG. 1.

DESCRIPTION OF THE FIGURE SHEETS

FIGS. 1A–1C provide the nucleotide sequence of a cDNA molecule or transcript sequence that encodes the kinase protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in the tissues showed in FIG. 1.

FIGS. 2A–2C provide the predicted amino acid sequence of the kinase of the present invention. (SEQ ID NO:2) In addition structure and functional information such as protein family, function, and modification sites is provided where available, allowing one to readily determine specific uses of inventions based on this molecular sequence.

FIGS. 3A–3K provide genomic sequences that span the gene encoding the kinase protein of the present invention. (SEQ ID NO:3) In addition structure and functional information, such as intron/exon structure, promoter location, etc., is provided where available, allowing one to readily determine specific uses of inventions based on this molecular sequence. 4 SNPs, including 1 indels, have been identified in the gene encoding the kinase protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a kinase protein or part of a kinase protein and are related to the thymidylate kinase subfamily. Utilizing these sequences, additional genomic sequences were assembled and transcript and/or cDNA sequences were isolated and characterized. Based on this analysis, the present invention provides amino acid sequences of human kinase peptides and proteins that are related to the thymidylate kinase subfamily, nucleic acid sequences in the form of transcript sequences, cDNA sequences and/or genomic sequences that encode these kinase peptides and proteins, nucleic acid variation (allelic information), tissue distribution of expression, and information about the closest art known protein/peptide/domain that has structural or sequence homology to the kinase of the present invention.

In addition to being previously unknown, the peptides that are provided in the present invention are selected based on their ability to be used for the development of commercially important products and services. Specifically, the present peptides are selected based on homology and/or structural relatedness to known kinase proteins of the thymidylate kinase subfamily and the expression pattern observed. Experimental data as provided in FIG. 1 indicates expression in the tissues showed in FIG. 1. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known thymidylate kinase family or subfamily of kinase proteins.

Specific Embodiments

Peptide Molecules

The present invention provides nucleic acid sequences that encode protein molecules that have been identified as being members of the kinase family of proteins and are related to the thymidylate kinase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the kinase peptides of the present invention, kinase peptides, or peptides/proteins of the present invention.

The present invention provides isolated peptide and protein molecules that consist of, consist essentially of, or comprise the amino acid sequences of the kinase peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the kinase peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated kinase peptide can be purified from cells that naturally express it, purified from cells that have been altered to express it (recombinant), or synthesized using known protein synthesis methods. Experimental data as provided in FIG. 1 indicates expression in the tissues showed in FIG. 1. For example, a nucleic acid molecule encoding the kinase peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/ cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the kinase peptides of the present invention are the naturally occurring mature proteins. A brief description of how various types of these proteins can be made/isolated is provided below.

The kinase peptides of the present invention can be attached to heterologous sequences to form chimeric or fusion proteins. Such chimeric and fusion proteins comprise a kinase peptide operatively linked to a heterologous protein having an amino acid sequence not substantially homologous to the kinase peptide. "Operatively linked" indicates that the kinase peptide and the heterologous protein are fused in-frame. The heterologous protein can be fused to the N-terminus or C-terminus of the kinase peptide.

In some uses, the fusion protein does not affect the activity of the kinase peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant kinase peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al, *Current Protocols in Molecular Biology*, 1992). Moreover, many expression vectors are commercially available that already encode a fusion moiety (e.g., a GST protein). A kinase peptide-encoding nucleic acid can be cloned into such an expression vector such that the fusion moiety is linked in-frame to the kinase peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the kinase peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data, Part 1*, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the kinase peptides of the present invention as well as being encoded by the same genetic locus as the kinase peptide provided herein. As indicated by the data presented in FIG. 3, the map position was determined to be on chromosome 2 by ePCR.

Allelic variants of a kinase peptide can readily be identified as being a human protein having a high degree (significant) of sequence homology/identity to at least a portion of the kinase peptide as well as being encoded by the same genetic locus as the kinase peptide provided herein. Genetic locus can readily be determined based on the genomic information provided in FIG. 3, such as the genornic sequence mapped to the reference human. As indicated by the data presented in FIG. 3, the map position was determined to be on chromosome 2 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a kinase peptide encoding nucleic acid molecule under stringent conditions as more fully described below.

FIG. 3 provides information on SNPs that have been found in the gene encoding the kinase protein of the present invention. SNPs were identified at 4 different nucleotide positions in introns. Such SNPs in introns may affect control/regulatory elements.

Paralogs of a kinase peptide can readily be identified as having some degree of significant sequence homology/identity to at least a portion of the kinase peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a kinase peptide encoding nucleic acid molecule under moderate to stringent conditions as more fully described below.

Orthologs of a kinase peptide can readily be identified as having some degree of significant sequence homology/identity to at least a portion of the kinase peptide as well as being encoded by a gene from another organism. Preferred orthologs will be isolated from mammals, preferably primates, for the development of human therapeutic targets and agents. Such orthologs will be encoded by a nucleic acid sequence that will hybridize to a kinase peptide encoding nucleic acid molecule under moderate to stringent conditions, as more fully described below, depending on the degree of relatedness of the two organisms yielding the proteins.

Non-naturally occurring variants of the kinase peptides of the present invention can readily be generated using recombinant techniques. Such variants include, but are not limited to deletions, additions and substitutions in the amino acid sequence of the kinase peptide. For example, one class of substitutions are conserved amino acid substitution. Such substitutions are those that substitute a given amino acid in a kinase peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gin; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant kinase peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as kinase activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the kinase peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a kinase peptide. Such fragments can be chosen based on the ability to retain one or more of the biological activities of the kinase peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the kinase peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in kinase peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the kinase peptides of the present invention also encompass derivatives or analogs in which a substituted amino acid residue is not one encoded by the genetic code, in which a substituent group is included, in which the mature kinase peptide is fused with another compound, such as a compound to increase the half-life of the kinase peptide (for example, polyethylene glycol), or in which the additional amino acids are fused to the mature kinase peptide, such as a leader or secretory sequence or a sequence for purification of the mature kinase peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a kinase-effector protein interaction or kinase-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, kinases isolated from humans and their human/mammalian orthologs serve as targets for identifying agents for use in mammalian therapeutic applications, e.g. a human drug, particularly in modulating a biological or pathological response in a cell or tissue that expresses the kinase. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte. A large percentage of pharmaceutical agents are being developed that modulate the activity of kinase proteins, particularly members of the thymidylate kinase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the tissues showed in FIG. 1. Such uses can readily be determined using the information provided herein, that which is known in the art, and routine experimentation.

The proteins of the present invention (including variants and fragments that may have been disclosed prior to the present invention) are useful for biological assays related to kinases that are related to members of the thymidylate kinase subfamily. Such assays involve any of the known kinase functions or activities or properties useful for diagnosis and treatment of kinase-related conditions that are specific for the subfamily of kinases that the one of the present invention belongs to, particularly in cells and tissues that express the kinase. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte.

The proteins of the present invention are also useful in drug screening assays, in cell-based or cell-free systems. Cell-based systems can be native, i.e., cells that normally express the kinase, as a biopsy or expanded in cell culture. Experimental data as provided in FIG. 1 indicates expression in the tissues showed in FIG. 1. In an alternate embodiment, cell-based assays involve recombinant host cells expressing the kinase protein.

The polypeptides can be used to identify compounds that modulate kinase activity of the protein in its natural state or an altered form that causes a specific disease or pathology associated with the kinase. Both the kinases of the present invention and appropriate variants and fragments can be used in high-throughput screens to assay candidate compounds for the ability to bind to the kinase. These compounds can be further screened against a functional kinase to determine the effect of the compound on the kinase activity. Further, these compounds can be tested in animal or invertebrate systems to determine activity/effectiveness. Compounds can be identified that activate (agonist) or inactivate (antagonist) the kinase to a desired degree.

Further, the proteins of the present invention can be used to screen a compound for the ability to stimulate or inhibit interaction between the kinase protein and a molecule that normally interacts with the kinase protein, e.g. a substrate or a component of the signal pathway that the kinase protein normally interacts (for example, another kinase). Such assays typically include the steps of combining the kinase protein with a candidate compound under conditions that allow the kinase protein, or fragment, to interact with the target molecule, and to detect the formation of a complex between the protein and the target or to detect the biochemical consequence of the interaction with the kinase protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant kinases or appropriate fragments containing mutations that affect kinase function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) kinase activity. The assays typically involve an assay of events in the signal transduction pathway that indicate kinase activity. Thus, the phosphorylation of a substrate, activation of a protein, a change in the expression of genes that are up- or down-regulated in response to the kinase protein dependent signal cascade can be assayed.

Any of the biological or biochemical functions mediated by the kinase can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the kinase can be assayed. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte.

Binding and/or activating compounds can also be screened by using chimeric kinase proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native kinase. Accordingly, a different set of signal transduction components is available as an end-point assay for activation. This allows for assays to be performed in other than the specific host cell from which the kinase is derived.

The proteins of the present invention are also useful in competition binding assays in methods designed to discover compounds that interact with the kinase (e.g. binding partners and/or ligands). Thus, a compound is exposed to a kinase polypeptide under conditions that allow the compound to bind or to otherwise interact with the polypeptide. Soluble kinase polypeptide is also added to the mixture. If the test compound interacts with the soluble kinase polypeptide, it decreases the amount of complex formed or activity from the kinase target. This type of assay is particularly useful in cases in which compounds are sought that interact with specific regions of the kinase. Thus, the soluble polypeptide that competes with the target kinase region is designed to contain peptide sequences corresponding to the region of interest.

To perform cell free drug screening assays, it is sometimes desirable to immobilize either the kinase protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of kinase-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a kinase-binding protein and a candidate compound are incubated in the kinase protein-presenting wells and the amount of complex trapped in the well can be quantitated. Methods for detecting such complexes, in addition to those described above for the GST-immobilized complexes, include immunodetection of complexes using antibodies reactive with the kinase protein target molecule, or which are reactive with kinase protein and compete with the target molecule, as well as enzyme-linked assays which rely on detecting an enzymatic activity associated with the target molecule.

Agents that modulate one of the kinases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of kinase protein activity identified according to these drug screening assays can be used to treat a subject with a disorder mediated by the kinase pathway, by treating cells or tissues that express the kinase. Experimental data as provided in FIG. 1 indicates expression in the tissues showed in FIG. 1. These methods of treatment include the steps of administering a modulator of kinase activity in a pharmaceutical composition to a subject in need of such treatment, the modulator being identified as described herein.

In yet another aspect of the invention, the kinase proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the kinase and are involved in kinase activity. Such kinase-binding proteins are also likely to be involved in the propagation of signals by the kinase proteins or kinase targets as, for example, downstream elements of a kinase-mediated signaling pathway. Alternatively, such kinase-binding proteins are likely to be kinase inhibitors.

The two-hybrid system is based on the modular nature of most transcription factors, which consist of separable DNA-binding and activation domains. Briefly, the assay utilizes two different DNA constructs. In one construct, the gene that codes for a kinase protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a kinase-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the kinase protein.

This invention further pertains to novel agents identified by the above-described screening assays. Accordingly, it is within the scope of this invention to further use an agent identified as described herein in an appropriate animal model. For example, an agent identified as described herein (e.g., a kinase-modulating agent, an antisense kinase nucleic acid molecule, a kinase-specific antibody, or a kinase-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The kinase proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the tissues showed in FIG. 1. The method involves contacting a biological sample with a compound capable of interacting with the kinase protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered kinase activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the kinase protein in which one or more of the kinase functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and kinase activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the tissues showed in FIG. 1. Accordingly, methods for treatment include the use of the kinase protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the kinase proteins. Antibodies can be prepared from any region of the peptide as described herein. However, preferred regions will include those involved in function/activity and/or kinase/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the tissues showed in FIG. 1. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the tissues showed in FIG. 1. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the tissues showed in FIG. 1. Thus, where a specific protein has been correlated with expression in a specific tissue, antibodies that are specific for this protein can be used to identify a tissue type.

The antibodies are also useful for inhibiting protein function, for example, blocking the binding of the kinase peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a kinase peptide or protein of the present invention (cDNA, transcript and genomic sequence). Such nucleic acid molecules will consist of, consist essentially of, or comprise a nucleotide sequence that encodes one of the kinase peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the kinase peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the kinase proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 2 by ePCR.

FIG. 3 provides information on SNPs that have been found in the gene encoding the kinase protein of the present invention. SNPs were identified at 4 different nucleotide positions in introns. Such SNPs in introns may affect control/regulatory elements.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in $Current\ Protocols\ in\ Molecular\ Biology$, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2×SSC, 0.1% SDS at 50–65 C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 4 SNPs, including 1 indels, have been identified in the gene encoding the kinase protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 2 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in kinase protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a kinase protein, such as by measuring a level of a kinase-encoding nucleic acid in a sample of cells from a subject e.g., mRNA or genomic DNA, or determining if akinase gene has been mutated. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte.

Nucleic acid expression assays are useful for drug screening to identify compounds that modulate kinase nucleic acid expression.

The invention thus provides a method for identifying a compound that can be used to treat a disorder associated with nucleic acid expression of the kinase gene, particularly biological and pathological processes that are mediated by the kinase in cells and tissues that express it. Experimental data as provided in FIG. 1 indicates expression in the tissues showed in FIG. 1. The method typically includes assaying the ability of the compound to modulate the expression of the kinase nucleic acid and thus identifying a compound that can be used to treat a disorder characterized by undesired kinase nucleic acid expression. The assays can be performed in cell-based and cell-free systems. Cell-based assays include cells naturally expressing the kinase nucleic acid or recombinant cells genetically engineered to express specific nucleic acid sequences.

The assay for kinase nucleic acid expression can involve direct assay of nucleic acid levels, such as mRNA levels, or on collateral compounds involved in the signal pathway. Further, the expression of genes that are up- or down-regulated in response to the kinase protein signal pathway can also be assayed. In this embodiment the regulatory regions of these genes can be operably linked to a reporter gene such as luciferase.

Thus, modulators of kinase gene expression can be identified in a method wherein a cell is contacted with a candidate compound and the expression of mRNA determined. The level of expression of kinase mRNA in the presence of the candidate compound is compared to the level of expression of kinase mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate kinase nucleic acid expression in cells and tissues that express the kinase. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte. Modulation includes both up-regulation (i.e. activation or agonization) or down-regulation (suppression or antagonization) or nucleic acid expression.

Alternatively, a modulator for kinase nucleic acid expression can be a small molecule or drug identified using the screening assays described herein as long as the drug or small molecule inhibits the kinase nucleic acid expression in the cells and tissues that express the protein. Experimental data as provided in FIG. 1 indicates expression in the tissues showed in FIG. 1.

The nucleic acid molecules are also useful for monitoring the effectiveness of modulating compounds on the expression or activity of the kinase gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in kinase nucleic acid expression, and particularly in qualitative changes that lead to pathology. The nucleic acid molecules can be used to detect mutations in kinase genes and gene expression products such as mRNA. The nucleic acid molecules can be used as hybridization probes to detect naturally occurring genetic mutations in the kinase gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the kinase gene associated with a dysfunction provides a diagnostic tool for an active disease or susceptibility to disease when the disease results from overexpression, underexpression, or altered expression of a kinase protein.

Individuals carrying mutations in the kinase gene can be detected at the nucleic acid level by a variety of techniques. FIG. 3 provides information on SNPs that have been found in the gene encoding the kinase protein of the present invention. SNPs were identified at 4 different nucleotide positions in introns. Such SNPs in introns may affect control/regulatory elements. As indicated by the data presented in FIG. 3, the map position was determined to be on chromosome 2 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a kinase gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant kinase gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the kinase gene in an individual in order to select an appropriate compound or dosage regimen for treatment. FIG. 3 provides information on SNPs that have been found in the gene encoding the kinase protein of the present invention. SNPs were identified at 4 different nucleotide positions in introns. Such SNPs in introns may affect control/regulatory elements.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control kinase gene expression in cells, tissues, and organisms. A DNA antisense nucleic acid molecule is designed to be complementary to a region of the gene involved in transcription, preventing transcription and hence production of kinase protein. An antisense RNA or DNA nucleic acid molecule would hybridize to the mRNA and thus block translation of mRNA into kinase protein.

Alternatively, a class of antisense molecules can be used to inactivate mRNA in order to decrease expression of kinase nucleic acid. Accordingly, these molecules can treat a disorder characterized by abnormal or undesired kinase nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the kinase protein, such as substrate binding.

The nucleic acid molecules also provide vectors for gene therapy in patients containing cells that are aberrant in kinase gene expression. Thus, recombinant cells, which include the patient's cells that have been engineered ex vivo and returned to the patient, are introduced into an individual where the cells produce the desired kinase protein to treat the individual.

The invention also encompasses kits for detecting the presence of a kinase nucleic acid in a biological sample. Experimental data as provided in FIG. 1 indicates that kinase proteins of the present invention are expressed in the tissues showed in FIG. 1. Specifically, in a pooled tissues of brain, heart, kidney, lung, spleen, testis, leukocyte. For example, the kit can comprise reagents such as a labeled or labelable nucleic acid or agent capable of detecting kinase nucleic acid in a biological sample; means for determining the amount of kinase nucleic acid in the sample; and means for comparing the amount of kinase nucleic acid in the sample with a standard. The compound or agent can be packaged in a suitable container. The kit can further comprise instructions for using the kit to detect kinase protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93:10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the kinase proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the kinase gene of the present invention. FIG. 3 provides information on SNPs that have been found in the gene encoding the kinase protein of the present invention. SNPs were identified at 4 different nucleotide positions in introns. Such SNPs in introns may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified kinase gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual*. 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterokinase. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding egions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory,* Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing finctions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as kinases, appropriate secretion signals are incorporated into the vector. The signal sequence can be endogenous to the peptides or heterologous to these peptides.

Where the peptide is not secreted into the medium, which is typically the case with kinases, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of vectors and host cells

The recombinant host cells expressing the peptides described herein have a variety of uses. First, the cells are useful for producing a kinase protein or peptide that can be further purified to produce desired amounts of kinase protein or fragments. Thus, host cells containing expression vectors are useful for peptide production.

Host cells are also useful for conducting cell-based assays involving the kinase protein or kinase protein fragments, such as those described above as well as other formats known in the art. Thus, a recombinant host cell expressing a native kinase protein is useful for assaying compounds that stimulate or inhibit kinase protein function.

Host cells are also useful for identifying kinase protein mutants in which these functions are affected. If the mutants naturally occur and give rise to a pathology, host cells containing the mutations are useful to assay compounds that have a desired effect on the mutant kinase protein (for example, stimulating or inhibiting function) which may not be indicated by their effect on the native kinase protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a kinase protein and identifying and evaluating modulators of kinase protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the kinase protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the kinase protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, kinase protein activation, and signal transduction, may not be evident from in vitro cell-free or cell-based assays. Accordingly, it is useful to provide non-human transgenic animals to assay in vivo kinase protein function, including substrate interaction, the effect of specific mutant kinase proteins on kinase protein function and substrate interaction, and the effect of chimeric kinase proteins. It is also possible to assess the effect of null mutations, that is, mutations that substantially or completely eliminate one or more kinase protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a polypeptide comprising the amino acid sequence of SEQ ID NO:2;
   (b) a nucleotide sequence consisting of SEQ ID NO:1;
   (c) a nucleotide sequence consisting of SEQ ID NO:3; and
   (d) a nueleotide sequence that is completely complementary to a nuleotide sequence of (a)–(c).

2. A nucleic acid vector comprising the nucleic acid molecule of claim 1.

3. A host cell containing the vector of claim 2.

4. A process for producing a polypeptide comprising culturing the host cell of claim 3 under conditons sufficient for the production of said polypeptide, and recovering said polypeptide.

5. An isolated polynucleotide consisting of the nucleotide sequence set forth in SEQ ID NO:1.

6. An isolated polynucleotide consisting of the nucleotide sequence set forth in SEQ ID NO:3.

7. A vector according to claim 2, wherein said vector is selected from the group consisting of a plasmid, a virus, a bacteriophage.

8. A vector according to claim 2, wherein said isolated nucleic acid molecule is inserted into said vector in proper orientation and correct reading frame such that a polypeptide comprising SEQ ID NO:2 may be expressed by a cell transformed with said vector.

9. A vector according to claim 8, wherein said isolated nucleic acid molecule is operatively linked to a promoter sequence.

* * * * *

SEQUENCE LISTING

<160> NUMBER OF SEQ ID NOS: 4

<210> SEQ ID NO 1
<211> LENGTH: 2571
<212> TYPE: DNA
<213> ORGANISM: HomoSapien

<400> SEQUENCE: 1

```
cggggccgag ggcggcgtcg ctgaggcgcc catggccttc gcccgccggc tcctgcgcgg      60
gccactgtcg gggccgctgc tcgggcggcg cggggtctgc gctggggcca tggctccgcc     120
gtgccgcttc gtcctggagc ttcccgactg caccctggct cacttcgccc taggcgccga     180 cgccccggc gacgcagacg ccccgaccc ccgcctggcg gcgctgttgg ggccccggga      240
gcgcagctac tcgctgtgcg tgcccgtgac cccggacgcc ggctgcgggg cccgggtccg     300
ggcggcgcgg ctgcaccagc gcctgctgca ccagctgcgc cgcggcccct tccagcggtg     360
ccagctgctc aggctgctct gctactgccc gggcggccag gccggcggcg cacagcaagg     420
cttcctgctg cgcgaccccc tggatgaccc tgacacccgg caagcgctgc tcgagctgct     480
gggcgcctgc caggaggcac cacgcccgca cttgggcgag ttcgaggccg acccgcgcgg     540
ccagctgtgg cagcgcctct gggaggtgca agacggcagg cggctgcagg tgggctgcgc     600
acaggtcgtg cccgtcccgg agcccccgct gcacccggtg gtgccagact tgcccagttc     660
cgtggtcttc ccggaccggg aagccgcccg ggccgttttg gaggagtgta cctcctttat     720
tcctgaagcc cgggcagtgc ttgacctggt cgaccagtgc ccaaaacaga tccagaaagg     780
aaagttccag gttgttgcca tcgaaggact ggatgccacg ggtaaaacca cggtgaccca     840
gtcagtggca gattcactta aggctgtcct cttaaagtca ccacctctt gcattggcca     900 gtggaggaag atctttgatg atgaaccaac tatcattaga gagcttttt actctttggg     960 caattatatt gtggcctccg aaatagctaa agaatctgcc aaatctcctg tgattgtaga    1020
caggtactgg cacagcacgg ccacctatgc catagccact gaggtgagtg ggggtctcca    1080
gcacctgccc ccagcccatc accctgtgta ccagtggcca gaggacctgc tcaaacctga    1140
ccttatcctg ctgctcactg tgagtcctga ggagaggttg cagaggctgc agggccgggg    1200
catggagaag accaggaag aagcagaact tgaggccaac agtgtgtttc gtcaaaaggt    1260
agaaatgtcc taccagcgga tggagaatcc tggctgccat gtggttgatg ccagcccctc    1320
```

-continued

```
cagagaaaag gtcctgcaga cagtattaag cctaatccag aatagtttta gtgaaccgta    1380
gttactctgg ccaggtgcca cgtctaacta gattagatgt tgtttgaaac atctacatcc    1440
accatttgtt atgcagtgtt cccaaatttc tgttctacaa gcatgttgtg tggcagaaaa    1500
ctggagacca ggcatcttaa ttttacttca gccatcgtac cctcttctga ctgatggacc    1560
cgtcatcaca aaggtccctc tcatcatgtt ccagtgagag gccagcgatt gctttcttcc    1620
tggcatagta aacattttct tggaacatat gtttcactta atcactacca aatatctgga    1680
agacctgtct tactcagaca gcaccaggtg tacagaagca gcagacaaga tcttccagat    1740
cagcagggag accccggagc tctgcttct cctacactgg catgctgatg agatcgtgac     1800
atgcccacat tggcttcttc cacatctggt tgcactcgtc atgatgggct cgctgcatct    1860
ccctcagtcc caaattctag tagccaagtg ttcctgcaga ggctgtctat gtgtcctggc    1920
tgcccaaggg acactcctgc agagccattt tgggtaagg aacacttaca aagaaggcat     1980
tgatcttgtg tctgaggctc agagcccttt tgataggctt ctgatgtcat tcataaagac    2040
attcaagcca agatgctcca actgcaaata taccaacctt ctctgaatta tattttgctt    2100
atttatattt cttttctttt tttctaaaga attggctctg aatagaatgc acattttcca    2160
tctgaactgg atgcatatca tttagccaat ccagtaattt atttatatta atctatacat    2220
aatatgtttc ctcagcatag gagctatgat tcattaatta aaagtggagt caaaacgcta    2280
aatgcaatgt ttgttgtgta ttttcattac acaaacttaa tttgtcttgt taaataagtt    2340
caagtggatc ttggagtggg atttcttggt aaattatctt gcacttgaat gtctcatgat    2400
tacatatgaa atcgctttga catatcttta gacagaaaaa agtagctgag tgaggggaa     2460 attatagagc ttgtgtgact ttagggagta gctgtctctt atacacatac tcaagccctg    2520
aagccttgca tgtcctgcag cgtcgcacta aaggaggggg cttttgcacc c             2571
```

<210> SEQ ID NO 2
<211> LENGTH: 449
<212> TYPE: PRT
<213> ORGANISM: HomoSapien

<400> SEQUENCE: 2

```
Met Ala Phe Ala Arg Arg Leu Leu Arg Gly Pro Leu Ser Gly Pro Leu
 1               5                  10                  15

Leu Gly Arg Arg Gly Val Cys Ala Gly Ala Met Ala Pro Pro Cys Arg
                20                  25                  30

Phe Val Leu Glu Leu Pro Asp Cys Thr Leu Ala His Phe Ala Leu Gly
            35                  40                  45

Ala Asp Ala Pro Gly Asp Ala Asp Ala Pro Asp Pro Arg Leu Ala Ala
        50                  55                  60

Leu Leu Gly Pro Pro Glu Arg Ser Tyr Ser Leu Cys Val Pro Val Thr
65                  70                  75                  80

Pro Asp Ala Gly Cys Gly Ala Arg Val Arg Ala Ala Arg Leu His Gln
                85                  90                  95

Arg Leu Leu His Gln Leu Arg Arg Gly Pro Phe Gln Arg Cys Gln Leu
                100                 105                 110

Leu Arg Leu Leu Cys Tyr Cys Pro Gly Gly Gln Ala Gly Gly Ala Gln
            115                 120                 125

Gln Gly Phe Leu Leu Arg Asp Pro Leu Asp Asp Pro Asp Thr Arg Gln
        130                 135                 140

Ala Leu Leu Glu Leu Leu Gly Ala Cys Gln Glu Ala Pro Arg Pro His
145                 150                 155                 160
```

-continued

```
Leu Gly Glu Phe Glu Ala Asp Pro Arg Gly Gln Leu Trp Gln Arg Leu
                165                 170                 175
Trp Glu Val Gln Asp Gly Arg Arg Leu Gln Val Gly Cys Ala Gln Val
            180                 185                 190
Val Pro Val Pro Glu Pro Pro Leu His Pro Val Val Pro Asp Leu Pro
        195                 200                 205
Ser Ser Val Val Phe Pro Asp Arg Glu Ala Ala Arg Ala Val Leu Glu
    210                 215                 220
Glu Cys Thr Ser Phe Ile Pro Glu Ala Arg Ala Val Leu Asp Leu Val
225                 230                 235                 240
Asp Gln Cys Pro Lys Gln Ile Gln Lys Gly Lys Phe Gln Val Val Ala
                245                 250                 255
Ile Glu Gly Leu Asp Ala Thr Gly Lys Thr Thr Val Thr Gln Ser Val
            260                 265                 270
Ala Asp Ser Leu Lys Ala Val Leu Leu Lys Ser Pro Pro Ser Cys Ile
        275                 280                 285
Gly Gln Trp Arg Lys Ile Phe Asp Asp Glu Pro Thr Ile Ile Arg Arg
    290                 295                 300
Ala Phe Tyr Ser Leu Gly Asn Tyr Ile Val Ala Ser Glu Ile Ala Lys
305                 310                 315                 320
Glu Ser Ala Lys Ser Pro Val Ile Val Asp Arg Tyr Trp His Ser Thr
                325                 330                 335
Ala Thr Tyr Ala Ile Ala Thr Glu Val Ser Gly Gly Leu Gln His Leu
            340                 345                 350
Pro Pro Ala His His Pro Val Tyr Gln Trp Pro Glu Asp Leu Leu Lys
        355                 360                 365
Pro Asp Leu Ile Leu Leu Thr Val Ser Pro Glu Glu Arg Leu Gln
    370                 375                 380
Arg Leu Gln Gly Arg Gly Met Glu Lys Thr Arg Glu Glu Ala Glu Leu
385                 390                 395                 400
Glu Ala Asn Ser Val Phe Arg Gln Lys Val Glu Met Ser Tyr Gln Arg
                405                 410                 415
Met Glu Asn Pro Gly Cys His Val Val Asp Ala Ser Pro Ser Arg Glu
            420                 425                 430
Lys Val Leu Gln Thr Val Leu Ser Leu Ile Gln Asn Ser Phe Ser Glu
        435                 440                 445
Pro
```

<210> SEQ ID NO 3
<211> LENGTH: 20966
<212> TYPE: DNA
<213> ORGANISM: HomoSapien

<400> SEQUENCE: 3

```
aaaagttagg aagaagctgg tcttcctact taccctcaag gtgctcagtg gtgggaaata    60
gactggcacg tgactgtgga gtgtcaaggt ccgaggatac aaatagcctt ggtgggggac   120
acaggagagg ctactaaccc agatatgtgg ggggttatag ctatatcat gtcccccaaa    180
attcatgttc aggcctagcc cccagtgcct cacagtatga ctgtatttca aaataagcct   240
ttcaataggt gattacatta aaatgagaac attatgatgg gccctaaccc aatctgactg   300
gtgtccttcc cagaagagga aatttggaac ttcaaggaga cgccaaggat gcaagcacaa   360
aggaaaggtc ccgtgagaac acagagagaa ggaggcggtc tgcacgctag aaagagaggc   420
```

```
ctcagaaaaa gcaaaccctg ctggcaactt gatctccagc ttctctggcc acctgaactt    480
tgagaaaaca aattttctat tgtttaggcg gcccagtccg tggtattttg ttatggcagc    540
caggatagac taatacatcc agagaggtgg atggcatagg gaaaaggtca agcaggcttg    600
aggatgcagt actgtcttag agaagaaaag ggagtaacta aagactctt acttccatat     660 actacataca cgtgaaacca ccggtacatg ctaaatgtcc aaaagtgaaa ttcctgagaa    720
agaataaaaa ctattctatt ctcaaagagc taaaaatttt taaactccta attcttcttt    780
cttcttagcc tattaaccca cactccaacc acctatctat atttcacgtt tgttaagact    840
ttttttttca gaattaaata taatcccaag tttaagtcca atactattaa gacataaaaa    900
aaaaaactgc tttcagctca tctaatgttt tcaatcttcg tctcaattct attttttga    960 gagagtttcc ctggagaata ttatcttttt gtttgttttt ggtttgcttg acatcatttt   1020
taaaaggcat cagttaatga gtaaacacag aataaaatat ccaaataact gcgcaaacac   1080
tgttacactg ttaggcagtt acactgttag gcagcaacag tgctgatgct ggactgtggc   1140
aggcagaggt gctatcctg acacacttca ccttagtgca ggaaacttca atttggtgga    1200
agaaaggcga tttcgaggtt ccaatctggg cgacacttcc cagttggaga gtcagcaaaa   1260
gggagagggc aattccaaga agagggaaaa gcttgtgcac aggtgagtgt gtgcaaaggt   1320
gagtgtgtgc acaggtgagt gagtgcacag gtgagataag atacaggaga gggaagagcc   1380
agaactgcgc cctgttcccg caggaaagca gctctgcagg attagagggg cggggacgcg   1440
tggtcagagc taggagttga ggtcgggag ggagcccatg gtctgcaggg cctggtcagt    1500
catccaaggg cagtagtgcg cctgcaagtg ggcgttgaag agcccgttac accgggaagg   1560
gacttctctg tccctcgcgc gtgcaccccc gccccctcc atgcacccgg cataagccgc    1620
agaggaggaa ctcaaaccag ggtcgggggcc gccagccacc cgcagaacgc acacggagct   1680
accttggggc cgacggcgcg gggcctcatt cggtgtcagc cccgggagcc ggcgcctggg   1740
gaccgcgcag gcccgcggag ccgcgcacct ggggccccgg gccaagcgt ctgctcccga    1800 gcgccggccg tttatcgcgc acatctcgcg gcgaggagga gaggccggaa gggcgcccca   1860
gccccaaggc tcctgccccg cctgggcctc cggctttcgt ttccccgcaa cgcttcgctt   1920
tcgtttcccg ctggcgcctg gctccctccg ggtttcgttt cccgccggcg cctggctccc   1980
gccaggtttc gtttccgagg cggggccgag ggcggcgtcg ctgaggcgcc catggccttc   2040
gcccgccggc tcctgcgcgg gccactgtcg gggccgctgc tcgggcggcg cggggtctgc   2100
gctggggcca tggctccgcc gcgccgcttc gtcctggagc ttcccgactg caccctggct   2160
cacttcgccc taggcgccga cgcccccggc gacgcagacg ccccccgaccc ccgcctggcg   2220 gcgctgctgg ggccccgga gcgcagctac tcgctgtgcg tgcccgtgac cccggacgcc   2280
ggctgcgggg cccgggtccg ggcggcgcgg ctgcaccagc gcctgctgca ccagctgcgc   2340
cgcggcccct tccagcggtg ccagctgctc aggctgctct gctactgccc gggcggccag   2400
gccggcggcg cacagcaagg cttcctgctg cgcgaccccc tggatgaccc tgacacccgg   2460
caagcgctgc tcgagctgct gggcgcctgc caggaggcac acgcccgca cttgggcgag    2520 ttcgaggccg accgcgcgg ccagctgtgg cagcgcctct gggaggtgca agacggcagg   2580
cggctgcagg tgggctgcgc acaggtcgtg cccgtcccgg agccccgct gcacccggtg   2640 gtgccagact tgcccagttc cgtggtcttc ccggaccggg aagccgccg ggccgttttg   2700 gaggaggtaa gagttctgtc cgcttccagc tcccagcgtg gcatctgaac ccttcagacc   2760
agagaactgg accaagaggc tggtctgtaa agccggttct tgcctgggtg gtttgtttat   2820
```

-continued

```
ttccgttcac aaatcaggta gggaaggtgt cctgtatgcc aggcaactct tttaagattc    2880
ttgtttgcaa ggatcttcca acctgacgtg aacatagac ctacaccaag ccacgcgatg     2940
cttgctgtaa aagcatccca acagcagtac agagggagta aaggggctgc cgggagtgag    3000
ggaaaataat gtcagctggg aagtaatttt atttgctgat gatcaccatt caaggatctt    3060
ggggtgaaaa agaaaatgca tgagtttagg gggtttaaga aatttagact taaatagtgt    3120
ttacctaccg actggccatg aaccttgtgc aggttactca actactctaa gttttgccct    3180
ttgacatgta caattcccat cttgcgatgt tgtcctgatt aaggaaacat ctgactcaca    3240
gcaggtaccc acagaaagag actgaaaatt ctttctgatc gcaggctagg cagatgtcct    3300
cctgtgcacac agatgagccc tgaggatgcc cccatggatc ttgggaatat tttccaagct   3360
tacgggacag cgttgtggag cagttaagag tgcaaggtca accacgtgta tttaaattta    3420
aactctggca tttattagct gtgtcacttt gagcaagttt cttcaactct ctgcctcagt    3480
ttccttaatt catatggtgg gaataataat agcaccccccc ccacccccagt tcacagagat   3540
tggcaactga atacttgtaa agcacttaga agattgccat gctcagagca agcacataag    3600
tgtctgagcc tcgctctgag atgctgtgag cgtgcagtga gataatgcac attgaggaac    3660
tgggaattcc cagggggacg ctgctctgcc agcttcatga ttgcagtgct tggctgttta    3720
tctcagcccc ctgaatggct aggagaggac atgctgcaga tgaagactgc tctctccagc    3780
ccactgtgca gctgatttcc cattcttgtg acacagtgtt cccagcgggc ctgtagttcc    3840
atggttgcgg tgtcacagga cattgtgatg atgtgccttg cctggccttt ctcaaagctg    3900
ctcagtgaag gctgcaggcc accaagcgat ccagacaggg acagctgttt cgagccttgg    3960
ctgctcaata taaaataaaa tactccagtc catcctagca tcgaaatact ctgaattccc    4020
atggcctggc acagtgctca gtataactta ggccttatta gcatgcggca atattgtgct    4080
cagcaattta ggtgtgattt ctgcaaaagc cccctggctt cattgctgat ggatagacgt    4140
tgttttacag tgtacctcct ttattcctga agcccgggca gtgcttgacc tggtcgacca    4200
gtgcccaaaa cagatccaga aaggaaagtt ccaggttgtt gccatcgaag gactggatgc    4260
cacgggtaag ataatattac cttttagtta taggcaatga cactaactga ttagttgcag    4320
aaacagaaat acttcctgca aaaccaaact ttatatggag ccttatgtgt gcccctactg    4380
tgtggcaggc cctgtgctag gcaggccctg ggatgcagag atgaataaga ccttcaatat    4440
gaagcagcat gatgtgtggg cgcggatcct cagtgctctg gcggaacaca ggaagggcac    4500
tgaatctggc ctctgtgggg ctttgtcggg tggagtgcat ggtcaagggt gatacctgga    4560
ttgtattta agtacagata ggagttggtc aggtgatgaa agcaggtaac atcctccaga     4620
cagaagaaat agcctgggca aaggtgcagg ggcttgaacc agggtggtgt gtccaggaac    4680
cacaggcaat tcagagattc ttctggagca aaatgtggaa gaactaggaa atggaagaaa    4740
aaaaagcctt ctgagctgtc aaactgaggt caaaatataa tgtgtgctca catgagacca    4800
aagtacaaaa ggggcagaca tgctgctcct gtggcccagg acacactgag gagagggttg    4860
atgttggaga actagcatcc gagtggttca gcgtaggagt ttctcctcct gtgtaaactt    4920
gagggtaca gactttttaat aatataaaag gcaatttcca tatagaggta cttgtgaacc    4980
cagctaggga gatgtggcac aggtgatggc ccatgttgac catcctggct ccatgtgaag    5040
gagcgggcca tgtcctggcc ttcagggaga ccagctgtca tcactcaaat gtactggccg    5100
tgtccaggac ccatcacagt ttctttcagc tgcagaggga attgtaacac catcaatcct    5160
```

```
tcagctgatg tgttttgttg atcatttatt ttgtacccac agctaattta gatttggtgg      5220
gattacagga gacataaaaa ttcagcctca acacaagcat ccacacatac aaatgttaca      5280
aggagttagc atagagtggc agaaagaaca caggctagtg gttccgtctg ccctgcattt      5340
gcatcctgca ccaaggccta tcaggagggt gagtttgggt aaatttatta acttctccag      5400
tgctcaattt cttcttctgt cagatgatta ataataact gttttgcaga gtcactggga       5460
gaattaggag tataacgtgc tgagtacttg ctcctagca gacactgaga aatggtagct       5520
actgttaggg tccgtcctga aacctaaga aaaaagaaa atagatagtt ggcaataaag        5580
tgttaagtgt gtgatagaga aacttaaaaa taaatcgaaa cagtaggagc tcagagaaac     5640
tagtgcacag tgtgctggag tagatcttct catcaccacc tgtcctgagc tccaggcagc     5700
agctgagaat tgtgagatgg gctctgggaa gggactaatc tgtcacccga ggctgtgcaa     5760
gggggagtca gaaagtcaat gaggcctaag cagtgccttt gaggagaaag ctgaagccta     5820
aagcagatac aaaagctcta aaggccaagg ccaagcccaa aggggcaagc acaggagtga     5880
gtggtagaac cagggctgga aattggaaag ggattgcaca gaagtggaag cagggtatga     5940
agaaggtaga aagagaggag gggcgagaag agttgctgtg gatgccaggt gtgggttcat     6000
caactataga caataagagg agagaaagtc ttctgggttg gggacatggt aagagggtga    6060
gcagtagctg ggctgccggg aataaaagtc acacgtaaaa ggggctcttg tgtctagact    6120
cccaatatca gatttgatca ctaaccagaa ttttcctcc gggtttccta ataccacacg     6180
gagaaatcct aacttcctat gggtctacag cttttataa agaatcctgt tatttagtct     6240
actcatttca tttgcagttt gagagaacgt ctgtgctctt tctacgtcaa tgttaacttt    6300
ggggctgtgg ttaagatgta tatattttgt gtatgacctg caggtaaaac cacggtgacc    6360
cagtcagtgg cagattcact taaggctgtc ctcttaaagt caccaccctc ttgcattggc    6420
cagtggagga agatctttga tgatgaacca actatcatta gaagagcttt ttactctttg    6480
ggcaattata ttgtggcctc cgaaatagct aaagaatctg ccaaatctcc tgtgattgta    6540
gacaggtagg tataaagatg ccttgaatta ggcattttct ccctaatata taagtgtgtg   6600
tgtgtgtgtg tgtgtgtgtg tgtatacgta catgtatatg ccaggaaaaa aattgtgttt   6660
aagtcaaact gttattatga taataatagg aattctcctt atgaattgtt aattaccat    6720 accaggcatg gcatttgcta gagaattaca tatataatac tagtatctgg aactataact   6780
tgggtaggtg aatgttacat gttattccca gtttactgat gagaactata gatctcagaa    6840
aggtaaaata acttgccaag gtaagctgga aatagcatac cggggacatt aatgagtcta    6900
tactttcagt catttatttg ttcattggct tattcaacaa atacttactg gacacctcct    6960
gtgtgccaaa gactagtctc aatttagagg attcaatgat aaaccagtgt attagtccat    7020
tttcatgctg ctgataaaga catacccgag attcggcaat ttacaaaaga gagcagtta    7080 atggacttac agttccatgg ggctggggag gcctcacaat catggtggaa ggtacaaagc    7140
atgtctcaca tggcggcaga caagagtaga gagcatgtgc agggaaactc ccctttttaa    7200
aatcatcaga ccttgtgaga cttattcaca atcatgagaa cagcatggta aagacctgtc    7260
cccatgatgc aattacctcc cactgggtcc ttcccacaac acatgggaat tcaagatgag    7320
atttggatgg ggacacagcc aaaccatata actccactcc tggcctctcc caaatctcat    7380
gtcctcacat ttcaaaacca atcatgcctt accaacagtc ccacaactct taactcattt    7440
cagcattaac tcaaaagtcc acagccaaag tctcatctga gacaaggtaa gtctcttcca    7500
cctatgagcc tgtaaaatca aaagcaagtt agttatttcc tagatacagt gaggctacag    7560
```

```
gcattgggta aatacagcca ttacaaatga gagaaattga ccaaaacaaa ggggctacag     7620
gctccatgca agtctgaaat tcagctgggc agtcaaatct taaagctcca aaattatctc     7680
ctttgactct atttctcatg tccagatcat gctgatgcaa gaggtgggtc ctcatggtct     7740
tggacagctc catccctgtg ctttgcagg gtatagcccc cctccttgct gctttcacag      7800
gctggtgttg tctgcagctt ttccaggtgc atggtgcaag ctgtcagtgg atctaccatt     7860
ctggggtcta gtggacagtg gctctcttca aacagctccg ctaggtagtg ccccagtagg     7920
gactctgtgt tggggctcca accccacatt tcccttccac actgccctag cagaggttct     7980
ccatgagagc cccactcctg tagcaaactt ctgcctggac atccaggcat tccatacat      8040 cctctgaaat ctaggcggag gttcccaaac ctccattctt gacttctgtg tacctgtagg     8100
ctcaacacca catggaagct gccgaggctt ggggctttcc ccctctgaat caagagcctg     8160
agctgtacct tggcctctta ctcaaggcta gagtggctgg gacacagggc accaagtctc     8220
taggctgcac agagcagagg gaccctgggt ccacaaaacc atttttttcc ttctaaacct     8280
ctgggtctgt gatgggaggg gcagcagcag aggtctctga catgccctcg agacattttc     8340
cccattgtct tggtgattaa catttggctt ctcattgctt atgcaaactt ctgcagccag     8400
cttgaatttc tcctcagaaa atgggatttt cttttctgtc acattgtcag gctgcaaatc     8460
ttccaaactt ttatgctctg tttccatttt aaaaccgaat acctttaaca gcatccaagt     8520
cacctcttga atgctttgct gcttagaaat ttcttccacc agttacccta aattattctc     8580
tcaagttcaa agttccacaa atctctaggg caagggctaa atgccgccag tctctttgct     8640
aaagcataac aagagttacc tttgctccag ttctcaccaa gttcctcatt tccatctgag     8700
accacctcag cctggatttc attgtccata tcattatcag cattttggtc aaagccattg     8760
aacaaatctc tagggagttc aacctttccc acattttcct gtcttcttct aagccctcca     8820
gactgcttca acctctgtct attacccagt tccaaagttg cttccacatt tttgggtatc     8880
ttttcagcag caccccactt ctggtaccaa tttactgtac tggttcattt tcacactgct     8940
gataaagacg tacgagac tgggcaattt acaaagaaa gaggtttaat ggatttacag       9000
ttccatgtcg ctgaggaggt ctcacagtca tggtggaagt tacggcacat ctcacatggc     9060
agcagacaag agtagagagc ttgtgtaggg aaactcccct ttttaaaacc atcagatctt     9120
gtgagactta gtcactatca tgagaacagc atgggaaaga cctgcccctg tgattcaatt     9180
acctcccact gggtccctcc aacaacatgt gggaattcaa gatgagattt gagtgggatc     9240
acagccaaac catatcaatg agatagataa gtccctattt tcatggagca aacttaacat     9300
tataggagaa gaaaagtatc aggtgaacaa atacataaaa taatacataa gatgaggtaa     9360
gataatatca aagcatgata aatgcaggga agaggaaaaa tcaaagtaat gtgctaaaaa     9420
acggctaacc ctccactaga tatggtttag gaaggcctgt ctgagaaagc accattagtc     9480
agagccctga tttaaaaaaa aaaaggcaa atgtgaaaat tcccgggtta acagaaagca     9540
ctgtggagaa agaaatctgc aagaatgaag ctaagactga aataagctaa catatctgac     9600
aactagaaaa tgttatatgt tctgagaaca tagtagatgt ggaggtgctt tgtggatgaa     9660
tgggaagagg aaggttgggg caggtctgta gggcttgtag gccattcata gaatggattt     9720
tattctgagt gcactgggga gccattggaa tgtttctgat aaaggagaga cataaactga     9780
tttatacttt aaaaattcac ctgtaagaaa tagcttcact ttgggaggct gaggtgggcg     9840
gatcatgagg tcaggagatc gagaccatcc tggctaacac ggtgaaaccc cgtctctact     9900
```

```
aaaaatacaa aaaattagcc gggcgaggtg gtgggcactt gtagtcccag ctactcggga    9960
ggctgaggca ggagaatggc atgaacccca gggggtggag cctgcagtga gccgagatca   10020
tgccactgca ctccagcctg ggcgacacgc agactccgtc tcaaaaaaaa aaaaaaaaga   10080
aaagaaaaga aatagcttta ggtcaggtgc agtggctcac acctgtaatc caagcacttt   10140
ggaaggctga ggtgggaaga gtgcttgagc ccaagagttc aagaccagcc ttgataacat   10200
agtgagacct tgtctctaca aaaatatttt aaaaaaatag ctgggtatgg tggcacccac   10260
ttgtagtccc agctacttag gagactcagg aaggagaatc ccttaagccc aggaggtcga   10320
ggctgcaatg acaaagcaag aggatgacac agcaagaggg gccttgtctc aaaaaaaaaa   10380
aaaaaatccc aaaacaata aaacaaaaaa caaaaagaa gaaaaaaata gctttaaaaa    10440
tactataaga aagaggaaag gatatgacaa gcaggtcata ctgaacttac atcacgatga   10500
caaatggatg agaagattat agtcaccatg agattccatt ttactcccat ctggatttca   10560
ttttactccc ctccagttgg tgaaactact ataactaaag gtttcttcat atgatatgga   10620
tcaatagaaa ctctcatatg atgctagtca gaacatatca tatgatagta gcataatcac   10680
ttagagagca gtttgaaaag atgtagcaaa gtggaagatt gctcctgcct actgaagaaa   10740
cactcacaaa agtttctttc agcttccttc atactgttgc aaaatttgaa aaacctaaag   10800
cccatcaaca ggagaaagca taaataaata ccagcatatg tataaggtgg aaaaccatac   10860
agcagcagtg taaatatgtt gtgcaatgca tgagggcaca cacattacaa aaccgtaatg   10920
ttgaatgaaa atgtcaagtt gccaaaagat gtttattcag tagaatacat gcagttatcc   10980
atactgcaaa gagtagagag atgaaaggat gttgaacagc agatttaaga aagttgttct   11040
ctgggaagta gagataaatg tggttgataa ggagatcaga aggactttga ttgtgattgg   11100
attatttctt aacatttctt gaatgttcat tttctccaaa gatttactta tttttgtaaa   11160
cataagcaat tgcatttaag tatggcatag ttggtaaaga acattaatca taaatgtaaa   11220
tctcaaggaa tttcaagaag tgaacacagt caagtcacct gtacccagat caagaatgag   11280
agcctgccac agcccctaca cccctgttct gcccccaccc agtcactgcc catttcctcc   11340
ccaggggtag caactgtccc aactgccata gccatatatt agttctgcct gttcttaaac   11400
tgcctacaga tgcaactatt tgttaggtat ggagttttat ttgcacctga cttcttttcat  11460
accacatgtg ttttgaagat ttgcctgtgt tgttgtgaac taaatttttat gcattttttgg 11520
tgcacatatg gatgcagttc tgttacatag gttcccagga gcagaactgc agggcatgg   11580
ggtttgtggc tgttcaggtt tggtagatgt tgcaaaaagt attctaaaga ggttgaaaga   11640
atgttgagtc tcctcccctc cccacagcag tatttgccaa ttccctgtga ctaacagccc   11700
tgttgacatt agtattacca ggctttaatt ttgactcctc tagtttttcc acttgttcct   11760
ggtgggtaag ctggtcactg aaaagctgat ttgtcctatc tggacacaga actactactc   11820
cttcttgaa agtatatctt tttctgtaca cttttctgta tgtctgaaat attccatcaa    11880
gagaccaccc tgactgtatg tggagaataa agtgtgtggt gggggagggg caagaaagga   11940
aaaagaatca gctagaaggc tgtggctgca gtctaggctg tgatggccct tgagtagttt   12000
taatcctggg atgacaatag ggatggcaat ggggataaca ataataattt caaggttggc   12060
aagttacatg gaatcttagg atgaactgag aaggatacga aatcttgttc ctttatggga   12120
aggctttgcc tggaaaatgt ttttgcccta ttgttaacat gcccgatgtt atcatatgtg   12180
atatctgtat tagttctttc tcacactgct ataaagacgt acctgatact gggtaatcta   12240
taaagaaaag aggtttagtt gactgacaat tctgcatggc tatacgggag gcatggctgg   12300
```

```
ggaggcctca ggaaacttgc aatcatggtg gaaattgaag aggaaacaat ggcaacagga    12360
gagagagaga gagaggcagg ggcaggggca ggggcagagg cgagagagca gggggaagtg    12420
ctacacattt taaacaccca gatctcatga caactcacca tcacgagaac agcaaggggg    12480
gtgtctgccc ccatgatcca atcaactccc acagggcctc atctccaaca atgggaatta    12540
ttaggttggt gcaaaagtca ttgtggtttt tgatattatt attaatggca aaaccgcaa     12600 tgacttttgc accaacctaa tacccttttgg catgagattt tggtggggac aaagaaccaa   12660
accatattga catcttttttt gatacagtcc cctttatttc caagagaaag actaaggttt   12720
tcctagtagg gtatgacttt cgaggtccat tatgtcctag gatgcctgcg gatcctgaag    12780
cagcactggc cactgtgtgc aggcaggat ttctgcactc tgtcccccag ttttctgatc     12840
tgttaagtgg ggatactcat gccccttcc ctgcctactg tcaagagttg tgatgatgat     12900
tcagtgagtg gatgtgtgtg gaagtaccct gaaaatagga aattgctatt aaatataaa     12960 gcattattat atgagcagtg tataatgtgt tggcaaattg cttttgattt gaactaatgt    13020
ggcttccctg atagcaggag tggagaatac taaatagtgg gaagcatctg aaattgatgg    13080
gctaagggtg caattattta aaacaagcag ccgtattttc aatgggagaa ctctatagga    13140
aacaggtcct taattcttcc cttgatttgt cttctttgtg tgtgtgaatt gcctgcaatt    13200
tagttcttta aagaaatgct gtatcacctt gtcagatgaa agaaaagag cagttatttg     13260 ttgtctttgt ggattttatt catgtttaaa gattttaata aaatccatttt tagacagtac   13320 cattatctag ctgaaaaata tgagagacag taattttttaa cggggactgt ggttaaggtt   13380
ggagtcttaa tcacccccatt acctttaaaa atctattctt gctggtgatt tttctacaat   13440
aaagaagact ttaaaaataa gataatatca gactctatat tcataggtag gtatttaatt   13500
caatgaatct ggagcatgtg ctgaccatgg tgtaaattat agtttaagta ccagaaaaag    13560
aaaactgaga ccctaattgg cttttttttga gcttgaggga caaaattcat ctggcagaga   13620
gagtgaaagt acaagtttgt gagtaacagg agttgggtaa gtaacacata ggaaggtgtc    13680
caggcagaat tcacaggagc tggcagtggc ctgaagctct cagagcacac ttttggaggt   13740
gaacaagggc tttgaaggat ggatggtgtt gagattatca actcccaagt gaattttttct   13800 ttttttttttt tagatgaagt ctcgctctgt tgcccaggct ggagtgcagt ggcgcgatct   13860
cggcacactg caagctctgc cttccgggtt cacgccattc tcctgcctca gcctcccgag   13920
tagctgggac tacaggtgcc cgccaccacg cccggctaat ttttttgtata tttagtaaag   13980 acggggtttc accatgttag ccaggatggt ctcgatctcc tgacctcgtg atccacccac    14040
ctcagcctcc caaccaagtg aatttttttac ttgtgtccctt ttcagtgctg tcctgtgttc   14100
tgttatcata atttgcaatg atccggcttt agttataacc agtgtctgat aagaattaga    14160
tatttatctt atagtaacag tgtgatacag tttttttttaa gcacttgtct gtatttgtaa   14220
caactatgga aggaaaacaa accttgcatg atctgtgttt tccagatgag gagatggagg    14280
ctatattagc ttagatgact tttacctaca tgtacaaaac aggtgggggcg ggggacacag   14340 gcagaataat gtacagttca ggtaacacag ggaatttatt atgtggatac cactgtgtac    14400
ttttcactgt ggagaggagt tcaattctaa aatgatcaaa attttaggat ttaaagaat     14460 tgggccgggc atggtaccct cacgcctgta attccagcact tgagaggcc aaggcgggtg    14520 gatcacctga ggtcaggagt ttgagaccag cctggccaac atgatgaaac ccatctcta     14580 ttaaaaatac aaaaattagc cgggcgtggt ggtgcatgcc tgtaatccca gctacttggg    14640
```

-continued

```
agggtggggc aggagaaatg cttgaacctg ggaagcaaag gttgcagtga gctgagatcg   14700
tgccactgca ctccagcctg ggcaacagag tgagactcca cctcaaaaca aaaataaagg   14760
attgaaggtg gtaatttgaa agtacaaatg aggaggggcc cctgggtatc tctacgttgg   14820
aatgtttata tcataaatat ttattgtgag tgatggtcct tttatattgg atctgaattg   14880
tccatttagt cctttaaaat tggaagatgg catgaacagg gcaagagtat aataaactat   14940
gctgataaat gaaatcgttc taattcattt attcatttat acacccaaat aacattcttt   15000
cattgcatat ctattatgtg ccagacatgc attactaaaa aagatttccc actcaagaaa   15060
ttacctaatg gaggagacaa tagatattac acttataaca gtagttctg atttgcaatg    15120 aggagttttt cagtagagtc acgtagaaag ggttttgaga gcacagagga gaaacagtc    15180 aattctgttt gggggcttcc taggagtctg aagggagagg agagttttgc tggctgagaa   15240
cctcactctc accagaggaa aagtaagca ggtgcagact aggagggatg ttctgtgtct     15300
taccagaaga ccaagcattt cctgtaggtt gtaggaagcc actaggcatt tttaaataga   15360
gactgatttg acttttgtgt atggtaataa ctttgttttc ctcccccaaa atcacttttt   15420
aaaacagcca gcagaaggag cgactgactt gcttaggag gactttcatg gagctgggca    15480
gggcatattt gtctccctgt ctcatactga ggcaccatca gcagactgga tagttgggag   15540
aaacaaagag gcttctacct cagggtccc agaatgtgaa tttcattggc aagttcaagt    15600
gaaaacagtg taggaactga catggccttt ccaggatttt agtctgccaa gacacagccc   15660
ttaaatacaa atgaactgcc aaacaggttc attgtcccct gtcaccctcc attctttcat   15720
agaggaatgc ggacagcagg accaaaaaga tgtgatgaca gaggggaggc cacactaaat   15780
ggtagtttga gatgggtcaa tggagctgtg tgaagaacac actgcattat tactgttgtc   15840
aattttattt tttaaacaat attgtataac tttttttagt ttataaaatt taattttatt   15900
taacttatgc aatactagaa aaacttctgt agagccaacc ctggtttcat cattcctggc   15960
tgctgatttt cagatgctac tttgacttct tctgcagaca gagaactcac taccccattc   16020
cttctcaggt actggcacag cacggccacc tatgccatag ccactgaggt gagtgggggt   16080
ctccagcacc tgcccccagc ccatcaccct gtgtaccagt ggccagagga cctgctcaaa   16140 cctgaccta tcctgctgct cactgtgagt cctgaggaga ggttgcagag gctgcagggc   16200
cggggcatgg agaagaccag ggaagaagca gaacttgagg ccaacagtgt gtttcgtcaa   16260
aagtaggtgt cccagtgcaa tgcaatgtga gcggcaggca ttcctgaagg gagatgaacc   16320
actggcactg gctttaggat tgtgaggaag tgatattgtt tccagttttc aaacacaaga   16380
gacaacatcc tctaagttac ttcagcccct tccaatgggc ttgtcaccac agggctgcag   16440
cattgttatc ttaaagcaaa ggtcatcgga ctagggatca gaccctgcca ctgatcctgg   16500
ctgtgctagg agcagctgca cctgggtaag acagtaagtg tctctgtgcc tcagtttccc   16560
cagtcatagt ataatcacac agagcactag ataacgagct catagtaaca tctacctatt   16620
agatgcttcc cgtgtgtcag gcattttact gatgttatgt catccttgtg aggaaaacat   16680
tagccgtatt ttacagttta caactttaag gctcaaagga ttaagtgatt tgtctaaatg   16740
tacataacta ttcactagta aaaccgggat taaaatcttt ctgattttgc agccagtgtt   16800
tttgttttaa ttagaaagtt ataaacacga ctgcagaaga gagtctggcc aggcctcctg   16860
cctcatgact gagtatgaat cagttctaca ccactgcctt taaaaactga agcagaaata   16920
ttttctctaa ctgaacaatg atagcccgt tatcataaca tagtaatgtt ataaataatg    16980
gtagctgctg tgggtaaaga tattatgtta agcaatttac ttgtattaat tccattaaac   17040
```

```
ttcagtgaac atttgcaagg aaggtacggt ttcagtcttc attttgcaga acaggaaact   17100
gagacacaga gaggagaaga gatttgacca attcacttgg ctaggaagtg gtcaggcaga   17160
gttgtgaatg cagacgatcc acctcgacac ccctatttta accacagtgc tataaggatt   17220
ccataaagaa acaggcacta gtcactctgt atacacatga aggctagcta gcatggaaag   17280
gatatgtaga tttctggcaa aatattagaa gagtcccatg catatattaa ggactgtggc   17340
ttgtatgaaa attattcagg gcacagactt gggggaaatt tgccactgaa caaattacct   17400
aaattctttg agcttcagtt gccttctctg caaaacaggg atgacaatag tcttccctcc   17460
taaggttact ttgagaatta aatgagaaaa atcatgcaaa atgctaatgc ttggcagaaa   17520
acaggtattc aacaagtgct agctattaaa cattattatt catttattat ttgttaaaca   17580
aaatgcatga acgtcttctg tgggcaaagc tagttacagt gagataaatg acatgggaag   17640
cttgcttcaa gctatttata ctatggtagg aaaagaacat taatgcaaat agctgtgtga   17700
aaaagtagac caactctttg tgttttgcct gtccccaggg tagaaatgtc ctaccagcgg   17760
atggagaatc ctggctgcca tgtggttgat gccagcccct ccagagaaaa ggtcctgcag   17820
acggtattaa gcctaatcca gaatagtttt agtgaaccgt agttactctg ccaggtgcc    17880 acgtctaact agattagatg ttgtttgaaa catctcacatc caccatttgt tatgcagtgt   17940
tcccaaattt ctgttctaca agcatgttgt gtggcagaaa actggagacc aggcatctta   18000
attttacttc agccatcgta ccctctttct gactgatgga cccgtcatca caaaggtccc   18060
tctcatcatg ttccagtgag aggccagcga ttgctttctt cctggcatag taaacatttt   18120
cttggaacat atgtttcact taatcactac caaatatctg gaagacctgt cttactcaga   18180
cagcaccagg tgtacagaag cagcagacaa gatcttccag atcagcaggg agaccccgga   18240
gcctctgctt ctcctacact ggcatgctga tgagatcgtg acatgcccac attggcttct   18300
tccacatctg gttgcactcg tcatgatggg ctcgctgcat ctccctcagt cccaaattct   18360
agagccaagt gttcctgcag aggctgtcta tgtgtcctgg ctgcccaagg acactcctgc   18420
agagccattt ttgggtaagg aacacttaca aagaaggcat tgatcttgtg tctgaggctc   18480
agagcccttt tgataggctt ctgagtcata taaaagacat ttcaagccaa gatgctccaa   18540
ctgcaaatat accaaccttc tctgaattat attttgctta tttatatttc ttttcttttt   18600
ttctaaagta tggctctgaa tagaatgcac attttccatt gaactggatg catttcattt   18660
agccaatcca gtaatttatt tatattaatc tatacataat atgtttcctc agcataggag   18720
ctatgattca ttaattaaaa gtggagtcaa acgctaaat gcaatgtttg ttgtgtattt    18780
tcattacaca aacttaattt gtcttgttaa ataagtacag tggatcttgg agtgggattt   18840
cttggtaaat tatcttgcac ttgaatgtct catgattaca tatgaaatcg ctttgacata   18900
tctttagaca gaaaaagta gctgagtgag ggggaaatta tagagctgtg tgactttagg    18960
gagtaggttg aaccaggtga ttacctaaaa ttccttccag ttcaaaggca gataaatctg   19020
taaattattt tatcctatct accatttctt aagaagacat tactccaaaa taattaaatt   19080
taaggcttta tcaggtctgc atatagaatc ttaaattcta ataaagtttc atgttaatgt   19140
cataggattt ttaaaagagc tataggtaat ttctgtataa tatgtgtata ttaaaatgta   19200
attgatttca gttgaaagta ttttaaagct gataaatagc attagggttc tttgcaatgt   19260
ggtatctagc tgtattattg gttttattta ctttaaacat tttgaaaagc ttatactggc   19320
agcctagaaa aacaaacaat taatgtatct ttatgtccct ggcacatgaa taaactttgc   19380
```

-continued

```
tgtggtttac taatctatgc tgtcatcctg ggtacatatt gatttgtctg aaaagtgctt     19440
tctcagattc ccctttaat attgtgatgt aaaggaggga aattttggta aaggaagttg     19500
aaaggtgtga gctggcaggc taagtggaat ttgtggtcag agtgctttca gagaaagggg     19560
agggctattg ttttatttta catatcattt cctcattaca aatattaaag acattttgta     19620
attcattctt tttacacctg gacttttat atactgatag gtatatatga cttacgagta     19680
ttttgtaaaa tagcacctcc taccctaaaa ctgatggcaa gtaaccettt gcttggctct     19740 gctcattgca agacgagctt tggttttgtt cctgtgatag accattagtt accccaaaat     19800
ttattcttcc tttcttccat ggtaatgtaa tatttagctt ggtacatggg tgccaataat     19860
tcctagtgca tttccaaggc tcccttaaca gctggaggtg ggcgactggc tagtttcttg     19920
ccaatagtat gtgagcagaa ggaatacctg aaatgtcaag gggatattat cactttcccc     19980
tttaactctt catatcggct gtattcagag gtgatagcca tctaaggacc aagagatgag     20040
gatgacacta aaaggaatta gcttgcctta ggtaaatagc aagggaaggg tccccagaga     20100
gccctcggcc caccagtcag tgcctcaccc cacataatgt aaaaagcagc ctggggaaaa     20160
aatcaagctg caggcactga taagggaact agcacagggt gttgtgcctg gagacatgcc     20220
tacggctgca cagataggag agcctctggc ccattcagat aaaagcttgc acaaacctct     20280
ggctcactca gatgagggaa caagtcctgg cataaaaaca cctttgtcct ttgtatagtc     20340
agcaggctcc caggaaaaag tttttttctc cttttgtggg cgtgggcaca gtgggctcca     20400
gttagttcca gtgggcactt tccttgccag tttttggact gtgagtctgg cctctgtgaa     20460
tcataacttc agcccctgat tggtcccagg caaaggtcct aggccaggct ttctgattgg     20520
tcctgggcca gggtgcctgg ccaagctgag tcatgccttc tccaagacag ccggtagact     20580
aagcacattc attcccctt ccagcccgta aaaccccac aactggcctc atagtgggca     20640
ccccattaga gctcccctt ctgctggcag agagcttct tttttcgctt attaaagttt     20700
cactccaact tcaccttgt tgtctgcact ccttaatctt cttggaatta ggacaaagaa     20760
ctctggatat tatctcagac aacgggagac tgttacatct tggtgcattg gtaagattac     20820
aacacatttt ggtgcattgg ctgggaagaa gggaattcat cagaaggatg attaagagtt     20880 gaccttttaac tttcacctttt acttgcattt ctgaggcttc ttgtctattc cagtctagtt     20940
tgctttcaca gagggcctag ccatca                                           20966
```

<210> SEQ ID NO 4
<211> LENGTH: 508
<212> TYPE: PRT
<213> ORGANISM: HomoSapien

<400> SEQUENCE: 4

```
Glu Cys Thr Ser Phe Ile Pro Glu Ala Arg Ala Val Leu Asp Leu Val
 1               5                  10                  15

Asp Gln Cys Pro Lys Gln Ile Gln Lys Gly Lys Phe Gln Val Val Ala
            20                  25                  30

Ile Glu Gly Leu Asp Ala Thr Gly Lys Thr Thr Val Thr Gln Ser Val
        35                  40                  45

Ala Asp Ser Leu Lys Ala Val Leu Leu Lys Ser Pro Cys Thr Ser Phe
    50                  55                  60

Ile Pro Glu Ala Arg Ala Val Leu Asp Leu Val Asp Gln Cys Pro Lys
65                  70                  75                  80

Gln Lys Gly Lys Phe Gln Val Ala Ile Glu Gly Leu Asp Ala Thr Gly
            85                  90                  95
```

```
Lys Thr Thr Thr Gln Gln Cys Thr Ser Phe Ile Pro Glu Ala Arg Ala
                100                 105                 110

Val Leu Asp Leu Val Asp Gln Cys Pro Lys Glu Val Gln Lys Gly Lys
            115                 120                 125

Phe Gln Val Ile Ala Ile Glu Gly Leu Asp Ala Thr Gly Lys Thr Thr
        130                 135                 140

Leu Thr Gln His Phe Lys Ser Leu Ser Arg Leu Ser Ser Tyr Ser Arg
145                 150                 155                 160

His Pro Ser Cys Ile Gly Gln Trp Arg Lys Ile Phe Asp Asp Glu Pro
                165                 170                 175

Thr Ile Ile Arg Arg Ala Phe Tyr Ser Leu Gly Asn Tyr Ile Val Ala
            180                 185                 190

Ser Glu Ile Ala Lys Glu Ser Ala Lys Ser Pro Val Ile Val Asp Arg
        195                 200                 205

Tyr Trp His Ser Thr Ala Thr Tyr Pro Cys Ile Lys Phe Asn Tyr Val
    210                 215                 220

Ala Ser Glu Ile Ala Lys Glu Ser Pro Val Ile Val Asp Arg Tyr Trp
225                 230                 235                 240

His Ser Thr Ala Thr Tyr Pro Pro Cys Ile Lys Pro Val Glu Glu Asp
                245                 250                 255

Leu Leu Met Met Asn Leu Leu Ser Phe Glu Pro Phe Ile Leu Trp
                260                 265                 270

Ala Asn Tyr Leu Val Ala Ser Glu Ile Ala Lys Glu Ser Thr Asn Phe
            275                 280                 285

Pro Val Ile Val Asp Arg Tyr Trp His Ser Thr Ala Thr Tyr Ala Ile
        290                 295                 300

Ala Thr Glu Val Ser Gly Gly Leu Gln His Leu Pro Pro Ala His His
305                 310                 315                 320

Pro Val Tyr Gln Trp Pro Glu Asp Leu Leu Lys Pro Asp Leu Ile Leu
                325                 330                 335

Leu Leu Thr Val Ser Pro Glu Glu Arg Leu Gln Arg Leu Gln Gly Arg
            340                 345                 350

Gly Met Glu Lys Thr Arg Glu Glu Ala Glu Ala Ile Ala Thr Glu Val
        355                 360                 365

Ser Gly Gly Leu Gln Leu Pro Pro Ala His His Pro Val Tyr Gln Trp
370                 375                 380

Pro Asp Leu Leu Lys Pro Asp Leu Leu Leu Thr Val Glu Glu Arg
385                 390                 395                 400

Arg Leu Gln Gly Arg Gly Glu Lys Thr Glu Glu Ala Glu Ala Ile Ala
                405                 410                 415

Thr Glu Val Ser Gly Gly Leu Gln Tyr Leu Pro Pro Ala His His Pro
            420                 425                 430

Val Tyr Gln Trp Pro Gly Asp Leu Leu Lys Pro Asp Leu Val Leu Leu
        435                 440                 445

Leu Thr Val Asn Ser Glu Glu Arg Val Arg Leu Gln Gly Arg Gly
    450                 455                 460

Gln Glu Lys Thr Lys Glu Glu Ala Glu Leu Glu Ala Asn Ser Val Phe
465                 470                 475                 480

Arg Gln Lys Val Glu Leu Glu Ala Asn Val Phe Arg Gln Lys Val Glu
                485                 490                 495

Leu Glu Ala Asn Asn Val Phe Arg Gln Lys Val Glu
                500                 505
```